United States Patent
Ayres

(10) Patent No.: US 6,733,784 B1
(45) Date of Patent: May 11, 2004

(54) COATED, PLATFORM-GENERATING TABLET

(75) Inventor: James W. Ayres, Corvallis, OR (US)

(73) Assignee: The State of Oregon acting by and through the State Board of Higher Education on behalf of Oregon State University, Corvallis, OR (US)

( * ) Notice: Subject to any disclaimer, the term of this patent is extended or adjusted under 35 U.S.C. 154(b) by 0 days.

(21) Appl. No.: 10/334,835

(22) Filed: Dec. 31, 2002

Related U.S. Application Data

(62) Division of application No. 09/887,318, filed on Jun. 21, 2001.
(60) Provisional application No. 60/216,598, filed on Jul. 7, 2000.

(51) Int. Cl.[7] .............................. A61K 9/28; A61K 9/20; A61K 9/22; A61K 9/30; A61K 9/36
(52) U.S. Cl. ....................... 424/474; 424/400; 424/464; 424/465; 424/468; 424/475; 424/479; 424/480
(58) Field of Search .................................. 424/400, 464, 424/465, 468, 474, 475, 482, 484, 485, 486, 479, 480

(56) References Cited

U.S. PATENT DOCUMENTS

| | | |
|---|---|---|
| 4,839,177 A | 6/1989 | Colombo et al. |
| 5,256,440 A | 10/1993 | Appel et al. |
| 5,455,046 A | 10/1995 | Baichwal |
| 5,505,966 A | 4/1996 | Edman et al. |
| 5,545,413 A | 8/1996 | Kuczynski et al. |
| 5,656,294 A | 8/1997 | Friend et al. |
| 5,702,724 A * | 12/1997 | Stahl et al. .................. 424/465 |
| 5,766,623 A | 6/1998 | Ayres et al. |
| 5,783,212 A | 7/1998 | Fassihi et al. |
| 6,120,803 A * | 9/2000 | Wong et al. ................. 424/473 |
| 6,183,780 B1 * | 2/2001 | Van Balken et al. ........ 424/480 |

* cited by examiner

Primary Examiner—Gollamudi S. Kishore
Assistant Examiner—Simon J. Oh
(74) Attorney, Agent, or Firm—Klarquist Sparkman LLP

(57) ABSTRACT

An expanding tablet is described comprising a drug release controlling membrane material. After swallowing, the tablet hydrates and expands such that the membrane ruptures to directly expose some surfaces of the core tablet to hydrating and eroding liquids, thus generating in situ a tablet which is platform supported on non-exposed surfaces, and which releases active ingredient in approximately zero order fashion. More particularly, the dosage form is adapted for controlled release of various pharmaceuticals. A working embodiment of the tablet was a spray-coated tablet comprising a core having greater than 25% of an expandable material which expands upon exposure to an aqueous environment and at least one active ingredient, e.g., glipizide, and an outer rupturable coating surrounding the core comprising a rate release modifying membrane and a water-soluble modifier. A method for administering an active ingredient also is described. The method comprises (1) providing a tablet according to the invention, and (2) administering the tablet to a patient.

41 Claims, 19 Drawing Sheets

45% HPMC

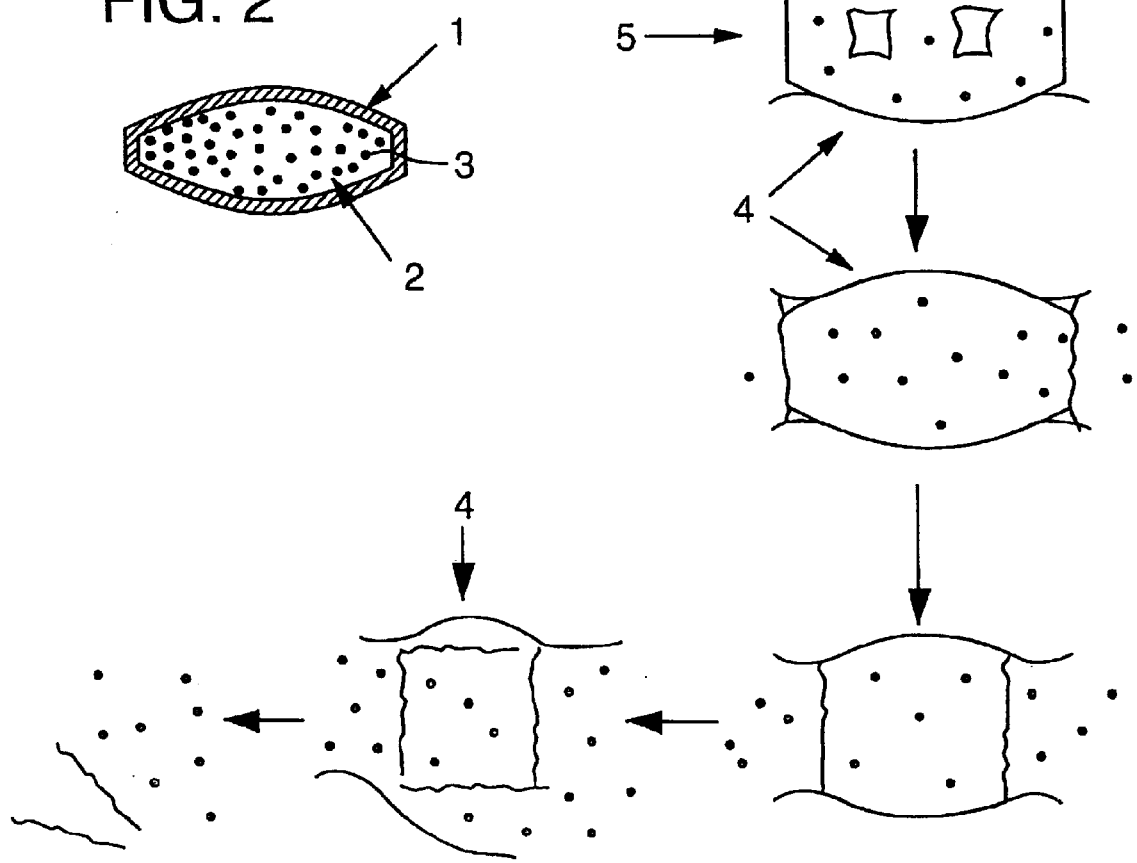

Dissolution Rate of Glucotrol XL 10 mg Tablets

Dissolution Rate of GSR 10 mg Tablets

Dissolution Profile Comparison among Glucotrol XL, GSR3 & GSR20

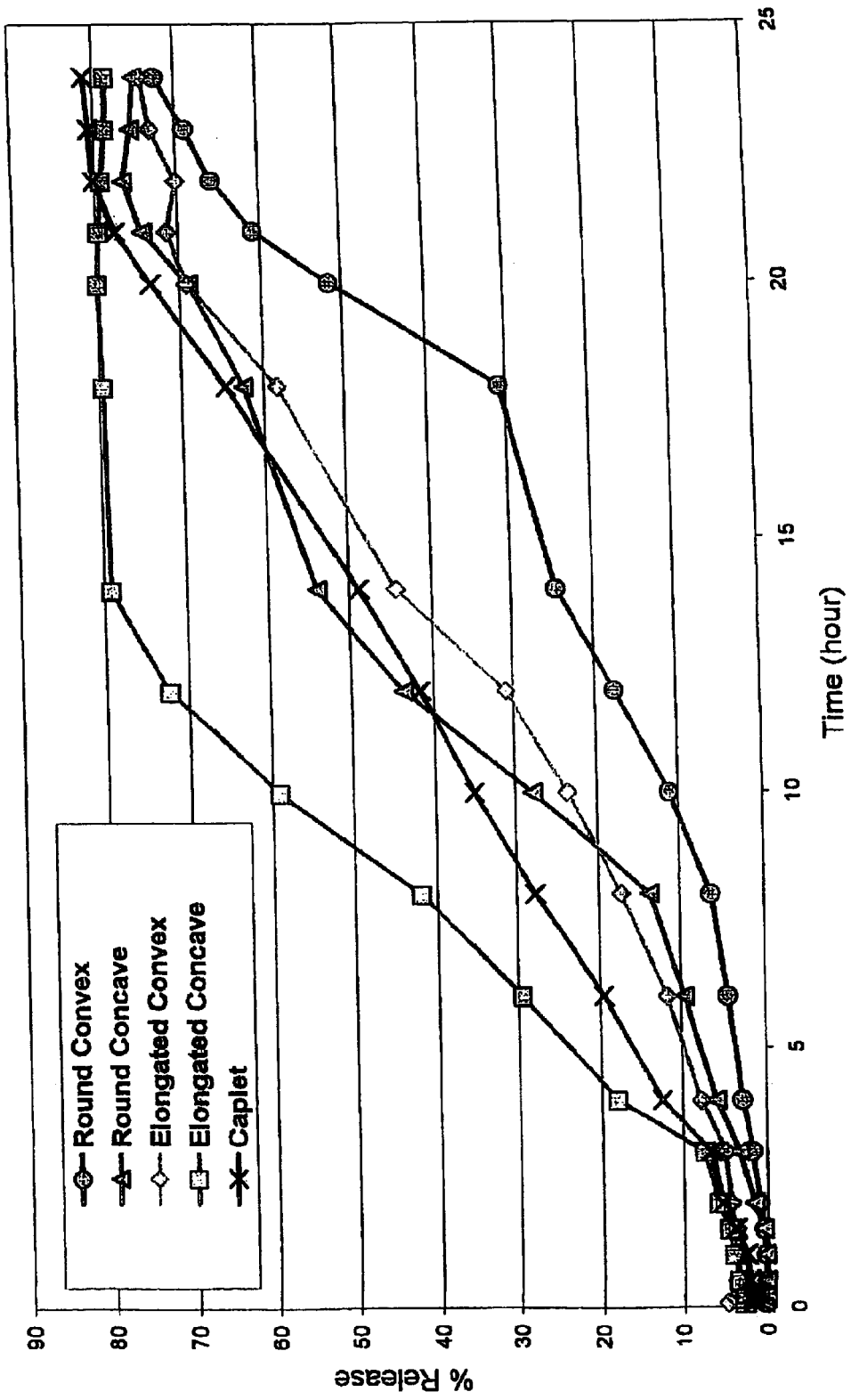
FIG. 13 Verapamil Tablets Dissolution Profiles

COATED, PLATFORM-GENERATING TABLET

CROSS REFERENCE TO RELATED APPLICATION

The present application is a divisional application of prior U.S. application Ser. No. 09/887,318, filed Jun. 21, 2000 which claims the benefit of the earlier filing date Jul. 7, 2000 of U.S. provisional application No. 60/216,598.

FIELD

This invention concerns a tablet adapted for controlled release of various pharmaceuticals.

BACKGROUND

Controlled release pharmaceutical dosage forms are commercially available. Zero order drug release from dosage forms is desired in order to provide a uniform and sustained drug delivery to a patient, but this is not easily achieved. Osmotic pump tablets are known (U.S. Pat. No. 5,545,413), and do a good job of providing zero order drug release. These tablets comprise a rigid coating membrane having an aperture formed therethrough using a laser. Gastrointestinal fluids penetrate the semipermeable coating membrane, and the core of the device generates sufficient pressure to force drug out through the laser-drilled aperture. These tablets generally provide a lag time of up to about two hours before beginning to release drug because some time is required for gastrointestinal fluids to penetrate the semipermeable coating membrane, and for the core of the device to generate sufficient pressure to begin forcing drug out through the aperture.

The osmotic pump tablets provide several advantages, including drug release which is independent of both pH and ionic strength. Moreover, drug release is not affected by erosion as a result of peristaltic gastrointestinal motion. Although these dosage forms provide zero-order drug release, they suffer from many problems in large-scale production. The semipermeable membranes which control water flow into the tablet, but block water flow out of the tablet, must be cast using organic solvents which are environmental pollutants closely regulated by the Environmental Protection Agency. This alone makes the process very expensive and undesirable. Moreover, laser equipment is required to drill the effluent hole in each tablet through which the drug must exit. Special equipment is required to position each tablet, one-at-a-time, correct side up, to drill the laser hole.

There also are problems associated with drug delivery using these osmotic pump tablets. For example, since drug can exit the tablet only through the aperture, any tablet which becomes trapped with the aperture against the gastrointestinal wall will pump drug directly into a localized spot on the mucous membrane. Thus, mucosal irritants, such as indomethacin and other non-steroidal anti-inflammatory drugs, should not be administered using osmotic pump tablets. Osmotic tablets do not release drug in some desirable ways, such as sustained fashion in the lower intestine, e.g., sustained colonic drug delivery without prior delivery of much of the drug in the upper gastrointestinal tract.

Hydrophilic-gum-matrix, controlled-release tablets are much easier to produce than osmotic pumps and provide sustained drug release. However, such tablets do not provide good zero-order drug release and cannot provide a lag time prior to drug release. These tablets do not provide pulsatile drug delivery. Further, hydrophilic gum matrix tablets undergo erosion in the gastrointestinal tract as a result of peristaltic activity such that drug release is much faster during times of high GI activity, which occurs with meals, than when the GI tract is quiescent, such as during fasting (Bertil Abrahamsson, Magne Alpsten, Gjom Bake, Ulf Jonsson, Maria Eriksson-Lepkowska and Annhild Larsson, "Drug Absorption from nifedipine hydrophilic matrix extended-release (ER) tablet-comparison with an osmotic pump tablet and effect of food", Journal of Controlled Release, 52, pp. 301–310 (1998)). There is no lag time for drug release from hydrophilic matrix ER tablets, and gastric erosion speeds up drug release to an undesirable extent as shown by Abrahamsson, et al.

A discussion of matrix tablet formation and difficulties associated with obtaining the desired drug release rate can be found in U.S. Pat. No. 5,783,212. This patent also points out problems with multilayer matrix tablets containing swellable layers which are not erodible, and erodible layers which are not swellable, including the lack of desired control over drug release rate from hydrophilic matrix gum tablets. U.S. Pat. No. 5,783,212 then describes multiple compression of at least three layers of swellable erodible polymers to form a tablet which controls drug release. U.S. Pat. No. 4,839,177 discloses multiple layer tablets containing a) a deposit-core of active substance, a high degree of swelling polymer and/or a swelling and gelling polymer and b) an aqueous insoluble support platform partially covering the deposit-core. The deposit-core tablet hydrates, swells, and erodes but the aqueous insoluble support platform remains attached to the core tablet for a prolonged time. These hydrophilic gum matrix tablets differ from known hydrophilic gum matrix tablets at least by virtue of their aqueous insoluble support platforms which leave at least one surface exposed and uncoated prior to administration. A particularly good review in this area is "Multi-layered hydrophilic matrices as constant release devices (Geomatrix Systems)", U. Conte, L. Maggi, P. Colombo, and A. La Manna, Journal of Controlled Release, 26 (1993) 39–47.

Conte, et al., identify the advantages of tablets described in U.S. Pat. No. 4,839,177 and point out the need to identify a method for industrial production of the devices described. The key to practicing the '177 patent is to only partially cover the tablet so there is at all times an uncoated area which allows drug to be released. However, this key feature is impossible to achieve using modern tablet spray coating chambers. Conte, et al., states that "the application by casting of an impermeable film on a portion of the matrix tablet could only be obtained manually. To overcome this drawback which does not allow for the automatic production of the system, different approaches were tried". That is, the key requirement for practicing the invention of only partially covering the tablet to expose a fixed portion of the tablet results in the impossibility of automatic production by casting or spray coating with impermeable films because such commercial processes cover the entire tablet. Thus, Conte, et al. used a multi-layer compression process known in the art to produce two layer tablets, three layer tablets, or even compression coated tablets which can produce a tablet completely surrounded by an outer compression coat. This process does allow automatic production of multi-layer tablets with characteristics of the '177 patent, but creates a new problem which is real and significant. That is, multiple layer tablets and compression coating both require special equipment which is very expensive and not widely available. And, such tablets are known to suffer from problems including splitting, cracking, or separation, especially the compression coated tablets. Coats of less than 1 mm are not possible because thinner coats crack at the core tablet edges. This coating thickness requirement can make an already large tablet too large to swallow.

Drug release from hydrophilic gum matrix core tablets partially coated by manual casting of an impermeable film (Conte, et al.) was described by the equation $Q/Q=kt^n$ where $Q/Q$=fraction of drug released at time t, k=kinetic constant, and n=exponent of drug release. When n=1, drug release is zero-order. The n values reported by Conte, et al. were 0.66, 0.64, 0.79, 0.84, and 0.76. Drug release is considered to be approximately zero order when the calculated n value for average dissolution results is greater than at least 0.70. Expected n values associated with drug release from an osmotic pump tablet are closer to 1.0. And, none of the partially covered, hand cast impermeable film coated matrix tablets provided a lag time prior to release of drug. Only the relatively difficult to produce compression coated core tablet was able to provide a lag time prior to drug release. The partially support coated tablets cannot be used for prevention of drug release in the stomach or upper small intestine.

Film coats have been applied to hydrophilic matrix tablets but they are not known to solve the problems described above. An extensive report, for example, presents coating effects on hydroxypropyl methyl cellulose tablets ["Application of a Barrier Film Coating to Achieve Zero-Order Release from Hydrophilic Matrix Tablets", R. J. Haluska, D. S. Helms and S. C. Porter, Proceedings of the International Symposium on Release of Bioactive Material, 19 (1992), Controlled Release Society, Inc.; "Application of Modified-Release Film Coatings to Hydrophilic Matrix Tablets in Order to Achieve Zero-Order Drug-Release Kinetics", Stuart C. Porter, $15^{th}$ Pharmaceutical Technology Conference, Christchurch College, Oxford, UK, Mar. $19^{th}$–$21^{st}$, (1996)]. A handout entitled "II. FILM COATING OF HYDROPHILIC MATRICES WITH AQUEOUS POLYMERIC DISPERSIONS: APPLICATION OF OPTIMIZATION TECHNIQUES" by Davis S. Helms describing these results in detail is available from Colorcon (West Point, Pa.). The following modified Korsmeyer equation was used to describe drug release: $M(t-1)/M(infinity)=k(t-1)^n$ where $M(t-1)/M(infinity)$=fraction of drug released at time t; k=kinetic constant; n=exponent of drug release; and 1=lag time. When n=1, drug release is zero-order. Based on experimentation, linear regression analysis, statistical validity checks, and iterations of the above, the authors teach that the following equations accurately describe drug release from the coated hydrophilic matrix tablets studied. n-value= 0.25+6.13 (Surelease amount)–5.49 (Opadry® amount)+ 2.03 (% HPMC)–0.15 ((% HPMC–0.125)/0.125)$^2$, and the n value can be higher than 0.9. Lag time=–0.3+10.7 (Surelease amount)–21 (Opadry amount)+1.0 (% HPMC)+ 0.007 (1/(0.101–Surelease amount)). The % drug released after 8 hours=110–335 (Surelease amount)+481 (Opadry amount)–115 (% HPMC)–0.031 (1/(0.1005–Surelease amount))–0.12 (1/[(% HPMC–0.095)/0.095]$^3$). Helms et al. provide information concerning products having 0–25% HPMC. No information, nor predictive value, is provided by such studies at HPMC amounts greater than 25%.

These relationships resulted from observed drug release when the hydrophilic matrix tablet had from 0% to 25% hydroxypropyl methylcellulose (HPMC (Methocel K-4M, Dow Chemical)), and the tablets were coated with 0% to 10% weight gain of a coating containing from 0% to 40% of a water soluble, HPMC-based coating formula (Opadry®YS-1-7006, available commercially from Colorcon, West Point, Pa.) mixed with an aqueous ethycellulose-based dispersion (Surelease®, Colorcon). Surelease® is an insoluble, barrier coating widely used in coating drug containing tablets or beads to control drug release from the tablets or beads. Polymer-film-coated hydrophilic-matrix tablets reported by Helms, et al. have limitations, some of which are discussed below.

For once-a-day dosing of drugs it often is desirable to control drug release for more than 8 hours. Drug release from osmotic pumps often continues for longer than 15 hours, and may continue for 24 hours or longer. To sufficiently prolong drug release from hydrophilic gum matrix tablets in order to meet objectives, it currently is believed desirable to increase the amount of hydrophilic gum to over 30%, and more than 40% often is desirable. With only 25% HPMC in the core tablet, Helms, et al. report that increased modifier levels in the coating causes barrier coat failure, which results in no significant change in n-value or release profile when compared to uncoated standard. Barrier coat failure is undesirable. Barrier coat failure also occurs with coating weight gains below 4% as there is insufficient film coat strength to resist the swelling of the hydrophilic substrate. The situation is worse with 40% or more hydrophilic gum in the core tablet because swelling increases with increased hydrophilic gum.

It is known by those skilled in the art of tablet coating that barrier coat failure reported by Helms, et al., which results in no significant change in n-value or release profile when compared to uncoated standard, is unacceptable. Increasing barrier film coat thickness is the approach used to prevent barrier coat failure. But, Helms et al. also report that one potential undesirable effect of increasing barrier film coat thickness is that high levels of unmodified barrier coat can lead to unacceptably long lag times or even drug release "shut down" where the barrier coating becomes completely impermeable. Increasing modifier levels in the barrier coating helps prevent the barrier coat from being completely impermeable, but then barrier coat failure occurs.

Many hydrophilic gums swell more extensively than HPMC K-4M (Wattanaporn Tavipatana, "Bioadhesive Polymers in Drug Product Formulations", Doctor of Philosophy Thesis, Oregon State University, 1988). These other polymers can provide desired results in a hydrophilic matrix gum polymer tablet, but their extensive swelling results in increased failure of the barrier coat. Some non-limiting examples of such polymers include polycarbophil, polyethylene oxide, xanthan gum, sodium carbopol, and carboxymethyl cellulose. Some of these gums expand much more in intestinal fluid than in gastric fluid, e.g., xanthan gum, sodium carbopol, and polyethylene oxide 5,000,000. Triple layer compression of such tablets, or manually applying an impermeable film on a portion of the matrix tablet, could be used to modify and improve drug release patterns as taught by Conte, et al. But spray coating tablets having these extensively swelling materials is taught by Helms, et al., to result in barrier coat failure. If enough coating is applied to prevent barrier coat failure, then unacceptably long lag times or even drug release shut down occurs. Helms et al. is silent about the use and effect of mixtures of materials.

Even if HPMC is the hydrophilic polymer matrix gum in a core tablet, as the amount of HPMC is increased, the predicted n value decreases further and further below 1.0 (see equations of Helms, et al., above). This means that the release rate becomes less and less like zero order, i.e., goes away from the desired drug release pattern. Further, the expected drug release pattern according to Helms, et al., with more than 30–40% hydrophilic gum in the tablet, is such that the equations clearly show too much burst effect and overall the release of drug is incomplete in 24 hours, which means that less than the total amount of drug can be absorbed in the body. See, for example, FIG. 1 which is generated with the equations of Helms for various amounts of Surelease® rate controlling membrane containing 20% Opadry® modifier. Thus, it is desirable to increase the amount of hydrophilic gum to over 30%, and often to more than 40% to extend drug release to allow for once-a-day dosing, Helms teaches that drug release patterns from such formulations are undesirable.

Tablets containing high amounts of a hydrophilic gum are reported by Kim and Fasshi to achieve desirable zero-order drug release but these tablets do not achieve other desired objectives. Kim and Fasshi report preparation of tablets containing about 75%–90% hydrophilic gum materials. Each tablet was prepared one-at-a-time by weighing the necessary amount of powders, hand filling into a die, and compressing into tablets using a carver press. Using this common laboratory method, tablets prepared by combining HPMC and highly methoxylated pectin with drugs can provide nearly zero-order drug release in the USP dissolution apparatus, paddle stirring at 50 RPM (Hyunjo Kim and Reza Fasshi, Application of a Binary Polymer System in Drug Release Rate Modulation. 1. Characterization of Release Mechanism, Journal of Pharmaceutical Sciences, Vol. 86, No. 3, pp. 316–322, 1997; Hyunjo Kim and Reza Fasshi, Application of a Binary Polymer System in Drug Release Rate Modulation. 2. Influence of Formulation Variables and Hydrodynamic Conditions on Release Kinetics, Journal of Pharmaceutical Sciences, Vol. 86, No. 3, pp. 323–328, 1997; Hyunjo Kim and Reza Fasshi, A New Terinary Polymer Matrix System for Controlled Drug Delivery of Highly Soluble Drugs; I. Diltiazem Hydrochloride, Pharmaceutical Research, Vol. 14, pp. 1415–1421, 1997). These tablets exhibit no lag time and are sensitive to administration with food as taught by Abrahamsson, et al.

Highly methoxylated pectin was used by Kim and Fasshi because low methoxylated pectin is an anionic polysaccharide, and gelation of low methoxylated pectin is expected to be undesirably influenced by changes in gastrointestinal pH, which also would modify drug release rate. Pectin is the methylated ester of polygalacturonic acid, and typically is commercially extracted from citrus peels and apple pomace under mildly acidic conditions. A typical pectin molecule includes plural molecules of galacturonic acid connected in a linear chain, typically 300 to 1000 such molecules in a typical pectin molecule. The acid can be the free acid, or it can be an ester, such as a methyl ester, which is referred to as methoxylation, and different degrees of methoxylation can occur. For example, if 3 out of every 5 galacturonic acids are methoxylated, this then represents a degree of methoxylation of 3 out of 5, or 60 percent. "DM" or "DE" is short for degree of esterification. Both terms are interchangeable, and they refer to the percentage of acid groups which are present in the pectin molecule as the methyl ester. Any pectin which has a DE of 50% or more is referred to as high methoxy, or highly methoxylated, pectin, and any pectin which has a DE of less than 50% is referred to as low methoxy, or low methoxylated, pectin.

Highly methoxylated pectin gelation is not affected by such pH changes. Low methoxylated pectin reportedly requires the presence of calcium ions to gel. Gelation of pectin with calcium to produce small spheres designed for delivering drug into the colon has been described (U.S. Pat. No. 5,505,966). Other examples of required cross-linking agents in gums to control drug delivery exist. U.S. Pat. No. 5,455,046 describes matrix tablets composed of heteropolysaccharide gums and a homopolysaccharaide gum capable of cross-linking the heteropolysaccharide gum, plus a cationic cross-linking agent, such as calcium chloride, for sustained release of a medicament with a solubility of less than about 10 g/L. These cationic cross-linked gums may, in addition, also contain other acceptable gelling agents including vegetable gums, such as alginates, carrageenan, pectin, guar gum, xanthan gum, modified starch, hydroxypropyl methyl cellulose, and other cellulosic materials, so long as there is homopolysaccharaide gum capable of cross-linking said heteropolysaccharide gum plus a cationic cross-linking agent. The requirement for cross-linking often is undesirable because the reaction or agent may adversely affect drug stability or release.

Tablets described by U.S. Pat. No. 5,455,046 containing 50% xanthan gum/locust bean gum cross-linked with calcium (Compactrol) when coated to 5% weight gain of hydrophobic polymer (Surelease®) release drug consistent with no lag time and essentially no coating effect. The inventors state that the coated tablet "appears to be an acceptable 24 hour formulation. However, the results obtained indicate that acceptable 24-hour release formulations may be obtained with or without the hydrophobic coating" in cross-linked gums, meaning that the coating is not producing a lag time. Table 16 from this patent is reproduced below.

TABLE 16

FROM U.S. Pat. No. 5,455,046
Percent Dissolved

| Time (hr) | Ex 15 A | Ex 15 |
|---|---|---|
| 4 | 12.76 | 13.53 |
| 8 | 36.89 | 42.99 |
| 12 | 73.06 | 63.27 |
| 16 | 98.07 | 73.69 |
| 20 | 102.07 | 78.95 |
| 24 | 106.33 | 87.88 |

Many hydrophilic gum materials, including those used by Kim and Fasshi do not flow well in conventional tablet machine hoppers, and do not fill well into tablet dies. Tablet making experiments have shown that mixtures of HPMC and pectin powders sufficient to make up 95% of a 450 mg tablet did not flow well in commercial tablet machines and block or "bridge" in the hopper. Good tablets could not be made at very high speeds. It was necessary to utilize vibration-aided flow and reduced speeds. These tablets could be produced on a relatively small and slow scale for testing, but the formulation was not well suited for mass production. While these powders could be diluted with flow aids such as microcrystalline cellulose or fast flow lactose to produce a mixture suitable for compression on commercial tablet machines, the teachings of Kim and Fasshi show that such formulations have a drug release burst and are no longer linear while releasing drug, and drug is released over a shorter time when water-soluble additives are included in the formulation.

In summary, a need remains for a controlled-release tablet formulation which is relatively easy and inexpensive to produce using standard equipment, and which can easily be modified by the formulator to program drug release as desired. For hydrophilic matrix tablets, too little hydrophilic gum in the tablet results in drug release which is too fast overall, and too much hydrophilic gum results in too little drug release in a reasonable time. Coating on these tablets must be sufficiently thick and strong to prevent barrier coat failure, and still does not give the desired drug release. It has now been unexpectedly discovered that all of the above described problems can be easily overcome in preparation of suitable controlled release tablets.

SUMMARY

This invention concerns an expanding tablet to which coating has been applied to all exposed surfaces by spraying with a drug release controlling membrane material and, after swallowing, the tablet hydrates and expands such that the membrane ruptures mostly in only one direction to directly expose some surfaces of the core tablet to hydrating and eroding liquids, thus generating in situ a tablet which is platform supported on non-exposed surfaces, and which releases active ingredient in approximately zero order fashion. More particularly, the dosage form is adapted for controlled release of various pharmaceuticals.

Working embodiments of tablets according to the present invention comprise at least one expanding material, or a mixture of expanding materials, such as a hydrophilic polymer gum or mixture of hydrophilic polymer gums, in a matrix tablet which has been polymer film coated over the entire surface. Such tablets unexpectedly control drug release better than as described in U.S. Pat. No. 4,839,177 (Geomatrix tablet). There is no need to only partially cover the tablet, which means that application of an impermeable film on only a portion of the matrix tablet is no longer required to obtain the desired drug release. Thus, unlike U.S. Pat. No. 4,839,177, the present invention allows for automatic production. Manufacture is greatly simplified because standard equipment can be used and the core tablet can be coated over the entire surface in a standard tablet coating chamber. Relatively high amounts of hydrophilic gum matrix can be used and the time required to complete drug release can be controlled to occur over 24 hours, or faster if desired.

Importantly, drug release can be essentially equivalent to drug release from the more complex osmotic pump system, if desired. Embodiments of tablets according to the present invention can have a lag time like an osmotic pump tablet if desired, and release of drug occurs in a desired controlled release fashion. In some cases drug bioavailability is expected to be increased relative to drug bioavailability from an osmotic pump tablet. In one embodiment, a programmed release of drug is obtained by coating a tablet with additional drug either within the film coat or over the film coat, or in both places as needed to obtain a desired drug release profile. In this case, there may not be a lag time from the final tablet as drug release from the outer layer(s) may be so fast as to produce an immediate burst effect if desired, or the release may be sufficiently slow and short that the total release from the outer layer(s) in combination with delayed release from the film coated interior will be nearly zero-order beginning at time zero, or after a desired time.

A working embodiment of the tablet was a spray-coated tablet comprising a core having greater than 25% of an expandable material which expands upon exposure to an aqueous environment and at least one active ingredient, e.g., glipizide, and an outer rupturable coating surrounding the core comprising a rate release modifying membrane and a water-soluble modifier. The tablet also can include additional coating layers, such as an over coating of an active ingredient, or the rate release modifying membrane may be over coated or undercoated with an enteric coating material. The tablet can include a mixture of hydrophilic gum polymers, at least one of which is modified by enzymes in the intestinal tract, such as pectin or guar gum. Furthermore, the rate release modifying membrane may contain one or more active ingredients. Examples, without limitation, of rate release modifying membranes include ethyl cellulose or a methacrylate polymer containing modifiers, which influence active ingredient release.

Typically, the tablet includes a belly band, and at least a portion of the coating ruptures adjacent to or in the "belly band" area of the tablet upon exposure to an aqueous fluid, but the coating remains attached to some tablet surfaces as shown in the drawings. This produces a support platform in situ for drug delivery. Working embodiments of the tablets had belly bands between 1 and 8 mm thick and where the length of the tablet was at least 8 mm. Moreover, the belly band in initial embodiments typically was less than a vertical height of the tablet as measured at a center portion of the tablet.

Tablets according to the invention can be designed to have a drug-delivery lag time of from about 0.5 hours or more and less than or equal to about 6 hours. Preferably, the lag time is from about 1 to about 3 hours. Such tablets also can be designed to sustain release of an active ingredient following a lag time sufficient to provide therapeutically effective active ingredient concentrations when administered in a once- or twice-daily dosing regimen. Dissolution of an active ingredient from such tablets measured in vitro in a USP paddle stirring apparatus in appropriate aqueous media at 37° C., can substantially correspond to the following: from 0 to 5% of the total active ingredient is released after one hour, from 0 to 40% of the total active ingredient is released after four hours; from 20 to 80% of the total active ingredient is released after eight hours; and not less than 80% of the total active ingredient is released in 24 hours. The n value for such tablets typically is 0.7 or more from time of 10% active ingredient released until time of 75% active ingredient released, and preferably the n value is 0.85 or more from time of 10% active ingredient released until time of 85% active ingredient released.

Another embodiment of the tablet comprised one or more active ingredients, a mixture of hydrophilic gum polymers where the mixture comprises between about 40% and 85% by dry weight of the tablet ingredients, the mixture comprising at least one hydrophilic gum polymer which is modified by enzymes in the intestinal tract, such as pectin and/or guar gum, at least one excipient which promotes powder mixture flow, and a spray coating over the external surface of the tablet, the coating comprising a rate release controlling membrane.

Still another embodiment of the invention comprised a spray-coated tablet which exhibits a lag time for active ingredient dissolution. The tablet comprised glipizide, a mixture of hydrophilic gum polymers comprising at least one hydrophilic gum polymer which is modified by enzymes in the intestinal tract, and a rate release controlling membrane overcoating the mixture. For such tablets, at least one hydrophilic gum was hydroxypropyl methyl cellulose, the hydrophilic gum polymer which is modified by enzymes in the intestinal tract was pectin, and the rate controlling membrane comprised ethyl cellulose or a methacrylate. For such tablets having a first rate controlling membrane, the first rate controlling membrane may have been over coated with a second membrane. The second membrane could be added for a number of reasons, including aesthetic purposes, rate controlling purposes, enteric controlling purposes, or to add additional drug to the tablet. Moreover, the rate controlling membrane may have been over coated with one or more active ingredients which may be the same or different from the active ingredients in the core tablet, and release of the active ingredient may or may not have exhibited a lag time for active ingredient dissolution.

Still another embodiment of the tablet which exhibited a lag time for active ingredient dissolution comprised one or more active ingredients, a mixture of hydrophilic gum polymers comprising between about 40% and about 85% by dry weight of all tablet ingredients, the mixture comprising at least one hydrophilic gum polymer which is modified by enzymes in the intestinal tract and at least one excipient which promotes powder mixture flow and attracts water, and an outer rupturable coating comprising a rate release controlling membrane.

Still another embodiment of the invention comprised a barrier coated tablet which generates a support platform in situ. A drug dissolution versus time curve for such tablet indicated a lag time of between 1 and 3 hours, an n value of 0.85 or greater, and a k value between 0.04 and 0.25.

Still another embodiment of the invention comprised a barrier coated tablet which generates a support platform in situ, and a drug dissolution versus time curve with a lag time of between 1 and 3 hours, an n value of 0.85 or greater, and a k value between 0.05 and 0.1.

Still another embodiment of the invention comprised a core comprising an active ingredient, an enzymatically modifiable, expandable material which expands upon exposure to an aqueous environment, and an outer rupturable rate release modifying membrane, the tablet providing active ingredient release over at least a 16-hour period.

Still another embodiment of the invention concerns a tablet having a drug-delivery lag time having a core comprising an active ingredient, a water-soluble modifier gum, and at least one second expandable gum which expands upon exposure to an aqueous environment, and an outer rupturable rate release modifying membrane over coating the core.

The present invention also provides a method for administering an active ingredient. The method comprises (1) providing a tablet comprising a core having an active ingredient and an expandable material which expands upon exposure to aqueous environment, the core surrounded by an outer rate release modifying membrane which ruptures upon exposure to aqueous environment, and (2) administering the tablet to a patient.

BRIEF DESCRIPTION OF THE DRAWINGS

FIG. 2 is a cross sectional schematic view illustrating an embodiment of an active ingredient delivery system comprising an active ingredient in a spray coated expanding hydrophilic matrix.

FIG. 3 is a schematic drawing illustrating how the tablet of FIG. 2 generates support platforms in situ according to a current theory of operation.

FIG. 13 is a % release versus time curve for a Verapamil composition compressed into different tablet configurations.

DETAILED DESCRIPTION

Figure 1:
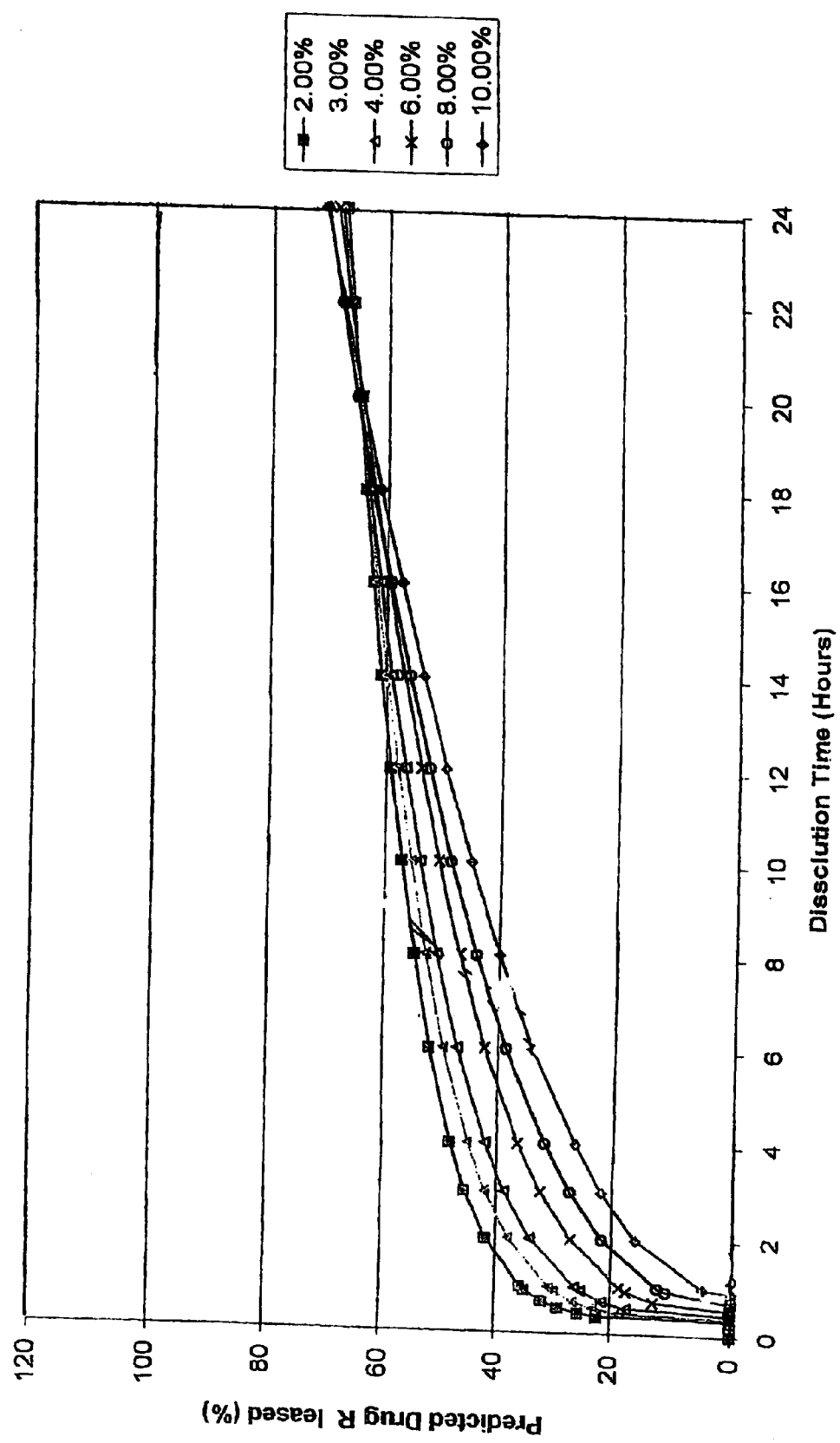
FIG. 1 is a graph showing predicted percent drug release versus time from zero to 24 hours for a core tablet containing 45% hydroxypropyl methyl cellulose coated with from 2% to 10% of a hydrophobic polymer containing a hydrophilic modifier according to the equations of Helms, et al.
Figure 4A:
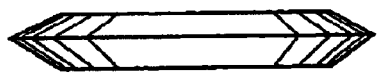
FIGS. 4A–4AB are schematic drawings illustrating possible non-limiting shapes of tablets which can generate variable areas of exposure and coverage by in situ generation of support platforms.
Figure 4B:
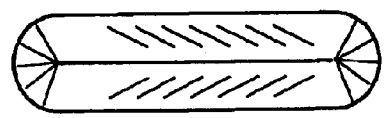
Figure 4C:
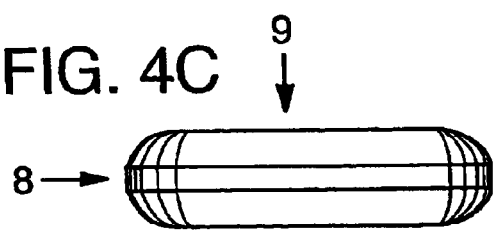
Figure 4D:
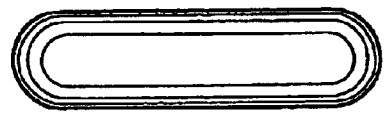
Figure 4E:
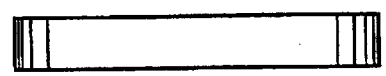
Figure 4F:
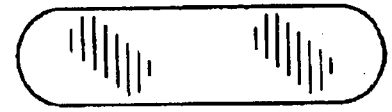
Figure 4G:
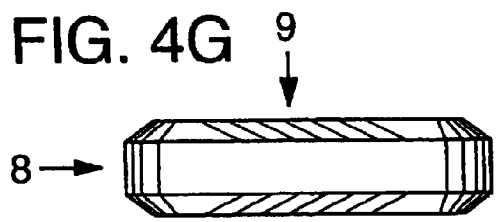
Figure 4H:
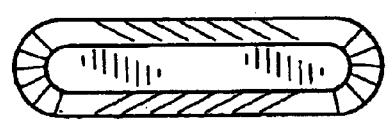
Figure 4I:
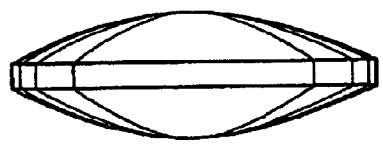
Figure 4J:
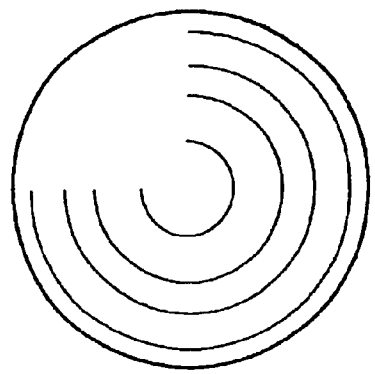
Figure 4K:
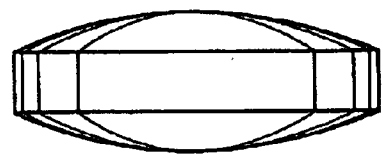
Figure 4L:
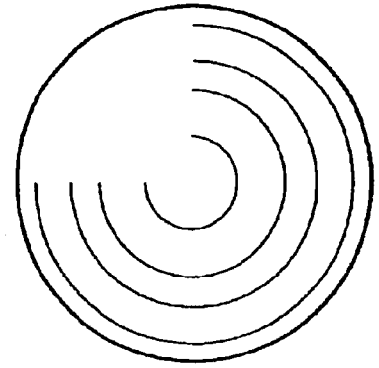
Figure 4M:
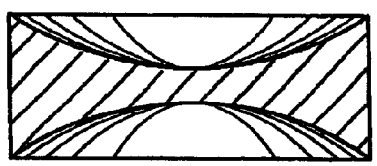
Figure 4O:
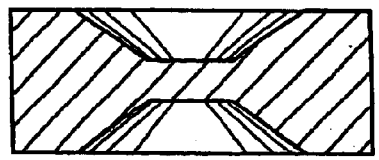
Figure 4N:
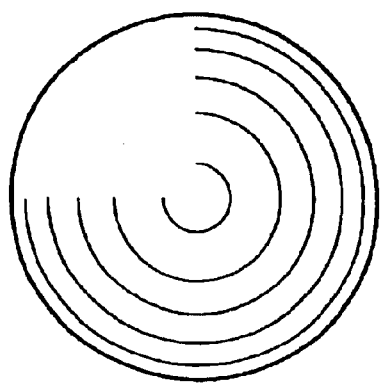
Figure 4P:
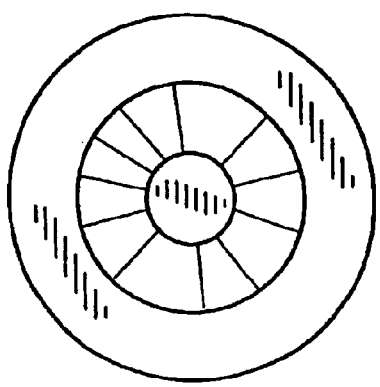
Figure 4Q:
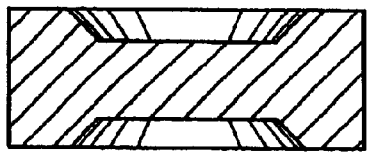
Figure 4R:
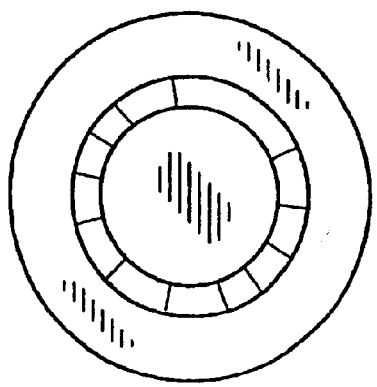
Figure 4S:
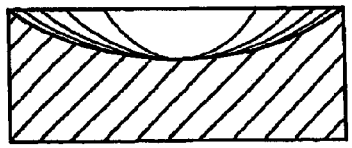
Figure 4U:
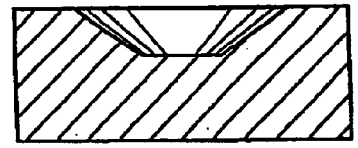
Figure 4T:
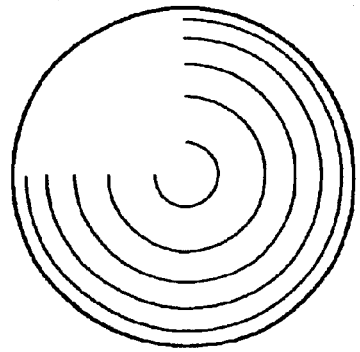
Figure 4V:
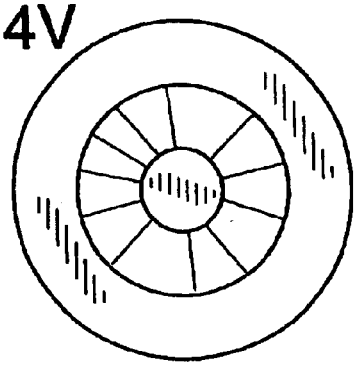
Figure 4W:
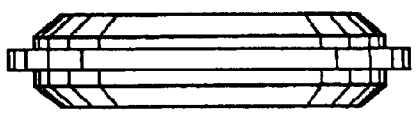
Figure 4X:
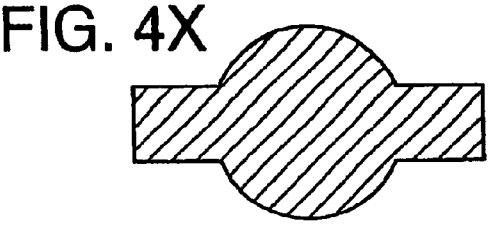
Figure 4Y:
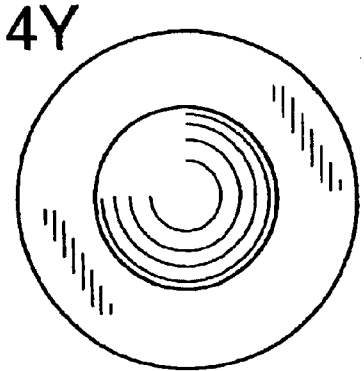
Figure 4A:
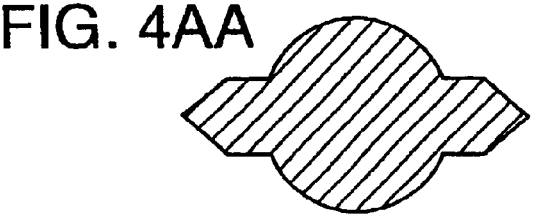
Figure 4A:
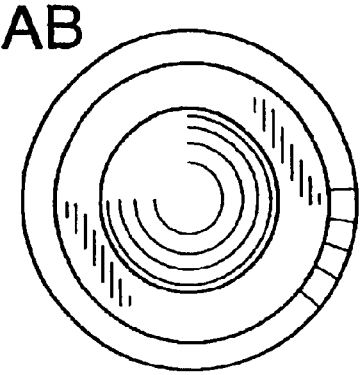

Terms and definitions are provided solely for the benefit of the reader, and should not be construed to limit the terms to any specific examples provided, or to be definitions which would be narrower than accepted by persons of ordinary skill in the art. Some non-limiting meaning of the following terms, for example, appear in my U.S. Pat. No. 5,766,623, which is incorporated herein by reference: active ingredients (includes active agents, therapeutic or diagnostic agents), spheres and equivalent terms, controlled release and equivalent terms including but not limited to sustained release and extended release, polymer coating agents, the concept of overcoating with a variety of excipients either with or without active ingredient, and hydrophilic gel forming materials or agents. Coating and overcoating are used interchangeably herein and refer to applying at least one coat, and perhaps plural coats, over a core compact, and core compact or core is used interchangeably with the term tablet.

Tablet is a term which is well known in the art, and is used herein to include all such compacted, or molded, or otherwise formed materials without limitation in terms of sizes or shapes, and all methods of preparation. Thus, as one common example, compressed or molded shapes which are known as caplets, are included.

Materials used as hydrophilic gel forming agents are generally the same as those described in U.S. Patent '623, incorporated herein by reference, and are often referred to herein as hydrophilic gums, which form a hydrophilic matrix tablet. In this case, hydrophilic gums or gel forming agents may be water-soluble materials, partially water-soluble materials, or water-dispersible materials, and include all substances which hydrate in an aqueous environment to form a sufficiently viscous consistency such that they are capable of at least partially influencing the rate of active ingredient release from the compressed compact but are not solely responsible for controlling release. This influence on release can be the result of diffusional control, erosional control, or combinations thereof. The coating polymer and the core tablet hydrophilic matrix gum in combination influence active ingredient release. And, hydrophilic polymers most suitable for this invention will swell sufficiently in the gastrointestinal tract such that a coating (overcoating) polymer film is ruptured to expose at least a portion of the tablet to the gastrointestinal fluids. As used herein, rupture is distinguished from traditional understanding of barrier coat failure in that the outcome of the loss of coat integrity when the tablet ruptures is part of the programmed drug release and is desirable. One feature which distinguishes coat rupture from coat failure is that when the coat ruptures as contemplated for the present invention subsequent drug release is still modified relative to the uncoated tablet. In contrast, once barrier coat failure occurs in terms of the present invention, subsequent drug release is not different from that of the uncoated material. Moreover, when rupture occurs, at least a portion of the coating remains adjacent to, and most likely adhered to, the core material, thereby forming a support platform. Most suitable polymer coating agents are those which are commonly used to spray-coat tablets to provide diffusional control, erosional control, or a combination thereof, of drug release from the tablet, and which can be mixed with water soluble materials to provide a coat which is sufficiently thick to modulate active ingredient release, and sufficiently thin, brittle or soft to burst when the core tablet swells while remaining as a support platform on some surfaces of the tablet for a prolonged period. Such coats can be called barrier coats, and any material included in the coat which influences any physical chemical characteristics of the coating including, but not limited to, diffusional resistance to drug passage are collectively referred to herein as film modifiers. Enteric coating polymers may be used as overcoats in some applications. The most preferred combination of hydrophilic gum matrix and polymer film coating material results in a tablet wherein the polymer coating has been applied by spray coating over the entire surface of the tablet and the tablet generates a support platform in situ. These concepts will be made clear through the examples and descriptions herein.

Lag time is defined as the time between when a tablet is placed into an aqueous environment and the time that active ingredient begins to be released from the tablet. The meaning of lag time is well known in drug dissolution literature. While not meant to be limiting, one way to measure lag time is to determine the amount of time before 5% of the drug dose is released from a device when the device is exposed to an appropriate aqueous environment in a United States Pharmacopeia paddle stirring dissolution apparatus operated at 50 rpm. An appropriate aqueous environment can include one or more than one aqueous media, including changes of media during the dissolution study, and often depends on the specific drug involved, and may or may not be prescribed in the United States Pharmacopeia as is well known to those skilled in the art. For this invention, the preferred appropriate media or medium is the one in which release of the active ingredient has an n value closest to 1.0, if the n value is sensitive to the medium used. Other known ways to calculate lag time are also appropriate and include, for example, by extrapolation of a linear or nearly linear, or initially nearly linear portion of a dissolution versus time curve to intersect the time axis. In this case, a lag time of more than 0.5 hours may be apparent even though up to 10% of the total dose may be released in the first 0.5 hours. Lag time can also be determined in vivo by deconvolution. A lag time of at least 0.5 hour or longer is considered to be important while a lag time of less than 0.5 hour is of little significance. Lag times of more than 4 hours are desired for delivery of drug into the lower portion of the small intestine while lag times of between 0.5 and 4 hours begin drug delivery in the upper regions of the gastrointestinal tract. Tablets of this invention often will be used to deliver drug in a once-a-day or twice-a-day multiple dosing regimen, and it generally will be desired that the lag time in vitro or in vivo be between about 1 and about 3 hours, the n value will be 0.85 or greater, and the k value will be between 0.04 and 0.25, and generally more preferable the k value will be between 0.05 and 0.1.

FIG. 2 illustrates one embodiment of a controlled release spray coated expanding tablet of this invention. The tablet comprises a film coat 1, a core tablet 2 and a drug particle 3. After the tablet is exposed to aqueous fluids in the gastrointestinal tract, fluids penetrate the polymer film coating 1 and the tablet contents swell. After sufficient swelling occurs, the polymer film coating 1 ruptures, generally in localized areas, such as the belly band region 5, as shown in FIG. 3, to expose at least part of the tablet 2. Surprisingly, coat rupture is fairly uniform in the belly band area such that the polymer film is not pulled off of the horizontal surfaces (reference numeral 4 in FIG. 3), but remains attached as support platforms to the horizontal surfaces of the tablet. During and after initial coat rupture, patches of coating may also be seen attached to the belly band area, but over time and up to 24 hours, these patches tend to leave the belly band area as shown in FIG. 3. With poor barrier coats which have been reported in the literature, for example such as those that contain too much hydrophilic material or those which are too thin, the coating film would be expected to dissolve or release from the tablet too quickly and expose all tablet surfaces.

As illustrated in FIG. 3, polymer coating rupture is programmed to be around the "belly band" area 5 of the tablet. After polymer coat 1 ruptures, support platforms 4 remain attached to the horizontal surfaces of the tablet. In 24-hour dissolution studies, the support platforms 4 remain attached for an extended period of time and can sometimes be seen sticking to remaining portions of the core tablet after 16 hours or more. Drug release occurs more rapidly from the exposed surfaces of the core tablet and drug release is slower or prevented from the surfaces which are still coated with the polymer film. The support platforms 4 have been generated in situ. This is quite different from what is known in the art such as U.S. Pat. No. 4,839,177, and from known use of diffusional control polymer film coats applied to core tablet formulations for the purpose of controlling drug release. In traditional terms, with respect to what is known in the art, the coatings 1 of this invention have been programmed to "fail". Following rupture failure of the coating 1 in one area of the tablet, the remaining support platforms 4 influence drug release by acting as a barrier, or at least a partial barrier, for release from the portion of the tablet covered by the support platform. In some cases, drug release rate following the lag time is equal to or even faster than drug release rate in uncoated tablets which is both unexpected and advantageous. This finding is unexpected since the barrier coat support platform is expected to decrease drug release rate. It is advantageous since drug bioavailability due to incomplete drug release is a problem with high content hydrophilic matrix tablets. The barrier coat composition and thickness, alone or in combination with tablet shape and formulation, can be modified to result in more or less effect of the support platform on drug release rate.

Prior to this disclosure, barrier coat failure would be considered unacceptable to one skilled in the art, and the problem would have been solved by using a hydrophilic gum which did not swell so much, or by increasing the coating thickness, or both. Helms, et al., state that there is no significant change in the n-value compared to control tablets when barrier coat failure occurs, no lag time for drug release, and that coats with more strength are required to prevent barrier coat failure. But, for the invention described herein, the rupture of the coat 1 in the belly band area 5 of the tablet with subsequent in situ generation of support platforms on the tablet can change the n value compared to uncoated tablets, does produce a lag time, and is not a barrier coat failure. Instead barrier coat rupture is a programmed effect designed to provide desired lag times plus controlled release of active ingredient from the tablet. It has been discovered that many formulation variables can be modified to control coat rupture and in situ generation of support platforms on specified areas of the tablet, and at the time desired as will become apparent herein.

FIGS. 4A–4K show different tablet shapes with different and variable belly band widths. Particular shapes can be used to influence the time to rupture of the polymer coat and the amount of exposed surface area of the swelling core tablet can be controlled in order to control drug release onset and rate from tablets of this invention. Polymer mixtures also can influence drug release. For example, polymer mixtures can be formed so as to provide programmed (i.e., pre-selected) coat rupture and therefore drug release. Initial coating failure may occur on sharp tablet edges, so rounded or sharp edges may be selected and formed to influence polymer coat rupture and subsequent amount of exposed surface area. A caplet shape which is about 20 mm long and 8 mm thick might have a belly band which is about 1 mm wide, or more up to the full width of the tablet (8 mm in this case). Or, the caplet may be shaped such that the belly band area is wider at the ends of the caplet than in the center such as would occur if the belly band area is the full width of the tablet, and the tablet is thicker at the ends than in the middle (bow-tie or dumbbell shaped tablet). The ratio of belly band width to tablet width may be from about 0.1 to 1.0 which, in combination with the core tablet and polymer coating material formulations will influence the rate at which the polymer coating material ruptures to generate in situ the support platform. In general, the diameter or length of the tablet will be larger than the thickness of the tablet, and the support platform generated in situ will be on the surfaces of the diameter or length of the tablet, and rupture of the coating polymer will occur in the belly band area. The shape of the tablet may be such that the belly band area protrudes from the tablet surface, or is flush with the tablet surface, or is depressed into the tablet surface (the latter case is more likely with a molded tablet than a compressed tablet). The shape of the belly band may be regular or irregular. Some belly bands, especially protruding belly bands, (see FIG. 4K for examples of protruding belly bands) may be rounded or flat or more pointed than rounded or flat, and in this case the ratio of belly band width to tablet width may be less than 0.1 and in the case exemplified by FIG. 4K having a pointed belly band the belly band width at the point is 0.0. Hydrophilic polymer gums can be selected based on their relative degree of swelling in gastric acid, or intestinal fluid, or both and it will now be appreciated that the rate and degree of swelling in combination with other factors described herein and known to one skilled in the art, such as drug solubility and ingredients chosen will influence the lag time and active ingredient release rate. Coating polymers may be essentially one material or mixtures of materials including either water soluble, or water insoluble (or somewhere in-between) modifiers, and may be applied as one coat or as multiple coats which are all the same or which differ from one another.

Degree of core tablet exposure and area of support platform coverage following in situ generation of the support platform are influenced by the relative shape of the tablet, among other things. All these parameters can be controlled in various combinations in order to influence the lag time and rate of active ingredient release. In one working embodiment of the present invention preferred case the shape of the tablet was round-convex, with a diameter of 11 mm, an overall height of 5 mm, and a thickness of 3 mm at the edges. The belly band width of this embodiment was also 3 mm, (full width at the tablet edges) to produce a ratio of belly band-to-tablet thickness at the edges of 1.0, and ratio of belly band over height of 0.6 (3 mm/5 mm). For round tablets, the diameter is the length.

In another working embodiment, the hydrophilic matrix gum mixture consists of hydroxypropyl methyl cellulose and pectin in a ratio of from about 9:1 to 1:1, and more preferable in the ratio of about 7:1 to about 2:1. It has now been found that these ratios can be manipulated to provide a mixture which can be combined with flow promotion aids, for example, fast flow lactose, dicalcium phosphate, or microcrystalline cellulose and other desirable excipients for making of tablets such that the combination can readily flow in a high speed tableting machine and readily form very acceptable compacted tablets with acceptable hardness and low friability. The desirable excipients may be water soluble or water insoluble. In a most preferred embodiment, the HPMC to pectin ratio is such that the active ingredient release is enhanced in the lower portion of the intestinal tract where pectinase enzymes can attack the pectin to speed up drug release, thereby helping prevent incomplete bioavailability, but the HPMC is in a sufficient amount to prevent complete dose dumping, i.e., release is controlled in a sustained fashion in spite of the pectinase action.

EXAMPLE 1

Figure 5:
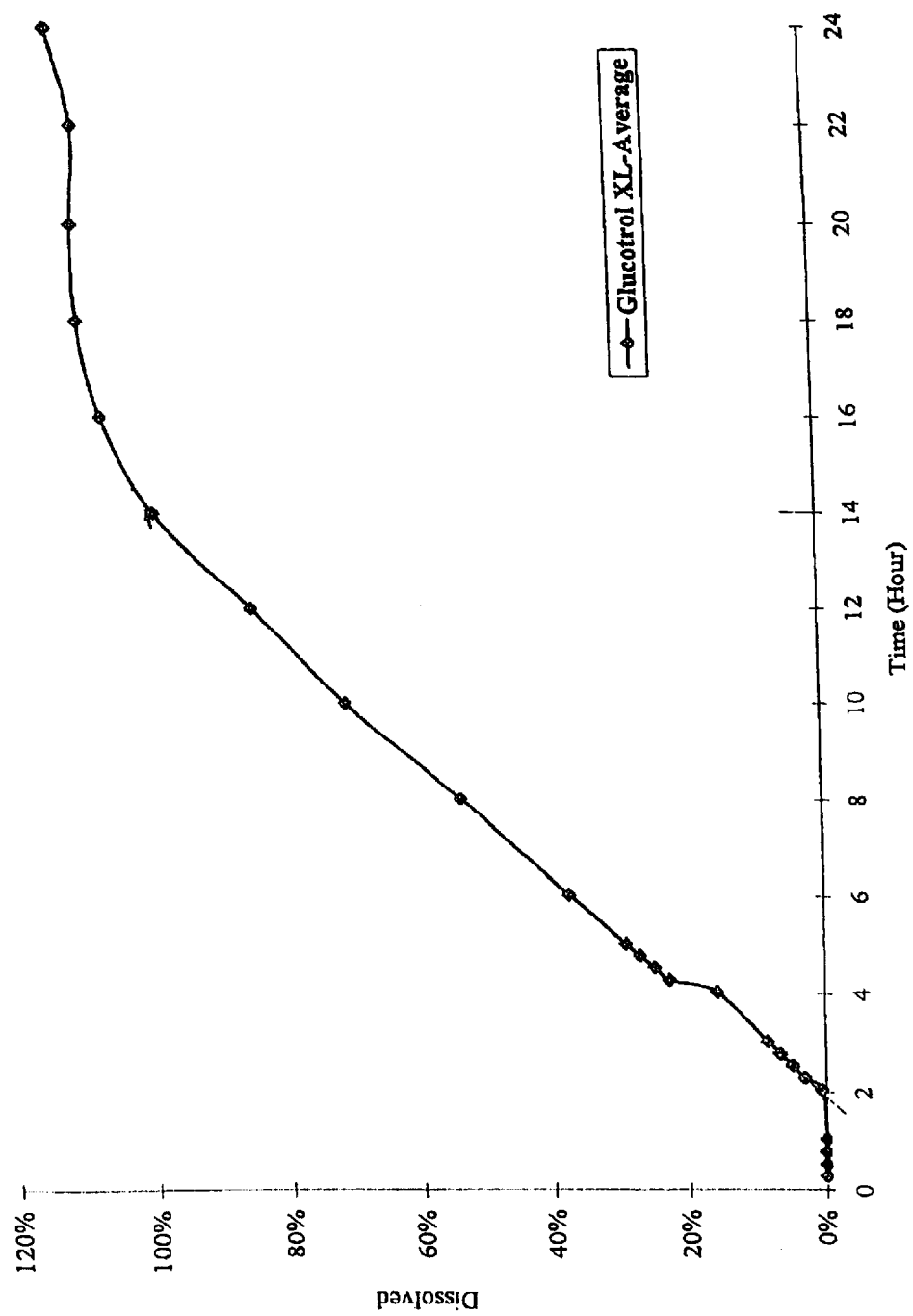
FIG. 5 is a graph showing percent drug (glipizide) release versus time from zero to 24 hours for Glucotrol XL osmotic pump tablets in a USP dissolution test apparatus.

Glipizide, a low solubility drug used to treat diabetics is commercially available in an osmotic pump tablet. The commercial product is Glucotrol XL available from Pfizer Corporation (New York, N.Y.). FIG. 5 shows the average dissolution of glipizide from six Glucotrol XL tablets in a United States Pharmacopeia dissolution apparatus. The dissolution medium was 800 ml of 0.1 N HCl for the first two hours, then 90 ml of 1 M K2HPO4 was added to adjust the pH to 5.8 for the next two hours, and then 10 ml of 6.5 M NaOH was added to adjust the pH to 6.8. The temperature was 37 degrees and a USP apparatus with paddle stirring at 100 RPM was used. These data show a lag time before dissolution begins of about 2 hours with a nearly linear release of drug over the next 12 hours. The n value for Glucotrol XL dissolution data from fitting with the Korsmeyer equation is 0.95 from the time of 2.5% dissolution until 100% dissolution.

EXAMPLE 2

FIG. 1 shows expected drug release from hydrophilic gum matrix tablets containing 45% HPMC which have been coated with from 2% to 10% of a polymer coating. The expected drug release lines in FIG. 1 were generated using the equations of Helms, et al. assuming that the polymer film was Surelease (ethyl cellulose) containing 20% Opadry (HPMC). The teaching of FIG. 1 is that for this type of coated formulation with 45% hydrophilic gum, the drug release vs. time curves are expected to be quite curved (n values 0.48 and smaller). The burst effect, incomplete release at 24 hours, and curvature in the drug release curve are well known and expected for hydrophilic gum matrix tablets. But, even though the shape of these curves is consistent with what is known about hydrophilic gum matrix tablets, it should be noted that the Helms, et al. equations are approaching mathematical failure in these calculations, and do fail mathematically when the amount of hydrophilic gum is over 48%. Prediction is for an initial release rate and burst effect to be so very fast as to approach infinity as the hydrophilic gum content in the core tablet approaches 48%. These equations fail if they are applied outside the range of hydrophilic gums studied and reported because physical and chemical processes generally cannot be applied outside the data collection boundaries. Such extended applications often result in nonsensical predictions. Equation failure confirms that the findings of Helms et al. cannot be applied outside the range of hydrophilic gums studied, i.e., cannot be extrapolated outside the data collection boundaries, notably not to tablets containing more than 25% hydrophilic gum or to gums or other materials with different expansion coefficients, for example.

Based on the composite teachings discussed herein, it is not expected that a hydrophilic gum matrix tablet can release drug in a pattern and over the length of time which is similar to that produced by Glucotrol XL osmotic pump tablet as shown in FIG. 5. Even more extended drug release is needed for once a day dosing of many drugs. Drug release from osmotic pumps is often longer than 15 hours, and may be 24 hours or longer. To sufficiently prolong drug release from hydrophilic gum matrix tablets in order to meet objectives, I have found that it is desirable to increase the amount of hydrophilic gum to over 35%, and more than 40% is often desirable. But, as the amount of HPMC is increased, the predicted n value may decrease further and further below 1.0 (see discussion, equations and figures) which means that the release rate becomes less and less like zero order, i.e., goes away from the desired drug release pattern. Further, the predicted drug release pattern with more than 40% hydrophilic gum in the tablet is such that there is either too much burst effect, or overall the release of drug is incomplete in 24 hours which means that less than the total amount of drug is expected to be absorbed in the body, and this condition is made worse if a barrier coat is applied which provides additional control to slow drug release further. If the burst effect in FIG. 1 did not occur, i.e., there was very little drug released during the first 2–4 hours, then the total drug released at 24 hours would be even less than what is predicted in FIG. 1.

EXAMPLE 3

Hydrophilic gum matrix tablet cores were made containing 45% hydrophilic matrix gum containing the following ingredients.

| Formula for 12000 Gengluco SR Tablets | | | |
|---|---|---|---|
| Glipizide | 10.30 mg | 2.29% | 123.60 gm |
| HPMC Type 2208 Viscosity 4000 | 67.50 mg | 14.99% | 810.00 gm |
| HPMC Type 2910 Viscosity 15 | 67.50 mg | 14.99% | 810.00 gm |
| Pectin | 67.50 mg | 14.99% | 810.00 gm |
| Avicel PH 102 | 176.50 mg | 39.20% | 2118.00 gm |
| Lactose Fast Flow | 52.00 mg | 11.55% | 624.00 gm |
| Magnesium Stearate | 9.00 mg | 2.00% | 108.00 gm |
| Total: | 450.30 mg | 100.00% | 5403.60 gm |

These tablets were given the name: Gengluco SR. They were prepared as follows:

1. Glipizide was mixed with HPMC 2910 (Viscosity 15) and USP grade Pectin (8.6% methoxy groups) and was then sieved through a #40 sieve (425 mm).
2. Pass HPMC 2208 (Viscosity 4000), Avicel and Lactose through a #40 sieve (425 mm) into the mixture of step 1.
3. Mix the contents of step 2 in a V-blender for 25 minutes.
4. Mix Magnesium Stearate plus Glyceryl Behenate with an equal volume of material from mixture of step 3 in a plastic bag, and pass through a #40 sieve (425 mm) into the remaining material from step 3.
5. Mix the contents of step 4 in a V-blender for 5 minutes.
6. Compress the bulk powder into 450.3 mg slightly concave tablets. (HATA press; Diameter of 11.1 mm; thickness of 5.1 mm at the center and 3 mm at the edge.)

Coating

1. Disperse Opadry white E-7-19101 (Colorcon Corp.) into stirring water, stir for 45 minutes.
2. Pour the suspension from step 1 into stirring Surelease suspension (Colorcon Corp.) and make up to target weight with water (see formula below).
3. Spray the coating solution onto core tablets made from Compression stage (weight gain 2.5%).

| 4. Parameters: | Inlet Air | 75~80° C. |
|---|---|---|
| | Outlet Air | 40~42° C. |
| | Coating machine: | Hicoater/Fruend. |

Surelease Film Formula (Solid Ratio=80% Surelease:20% Opadry white) 2.5% weight gain on the tablets= 135.1 g. A 0.25% excess is used for compensation of spraying loss.

| Surelease E-7-19010 (25% Solid Content) | 432.3 g |
|---|---|
| Opadry White 31K58901 | 27.0 g |
| Purified Water | 666.5 g |
| Total: | 1125.8 g |

Figure 6:
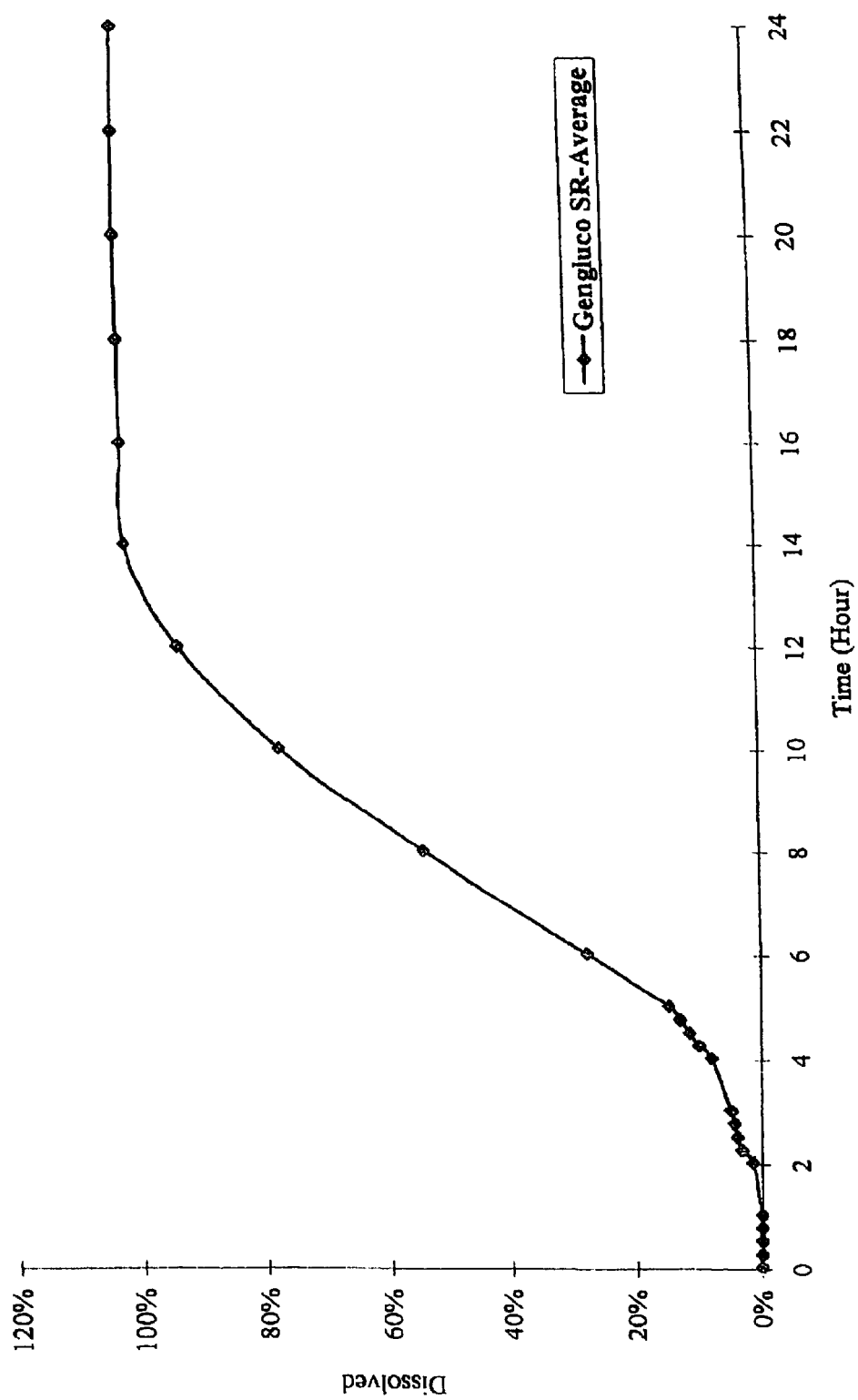
FIG. 6 is a graph showing percent drug (glipizide) release versus time from zero to 24 hours for Gengluco (in situ support platform generating tablet) tablets in a USP dissolution test apparatus.

FIG. 6 shows dissolution of glipizide from tablets made in this example using the dissolution conditions described in Example 1. It is clear that release of drug from hydrophilic matrix coated tablets of this Example 6 containing 45% hydrophilic matrix gum is quite different from the predicted theoretical release patterns for hydrophilic matrix tablets containing 45% hydrophilic gum as shown in FIG. 3. Data in FIG. 6 are quite similar to drug release from Glucotrol XL as shown in FIG. 5. These tablets were observed to behave as shown in FIG. 3, which shows the polymer film coating first visibly stretching, and then rupturing in the belly band area of the tablet, which resulted in the polymer film coating fitting on the top and bottom of the tablet somewhat like a baseball cap (support platform) on each of these areas with the center or belly band exposed. Initially, patches of coating material remain attached to the belly band area and slowly disappear or mostly disappear as the tablets continue to hydrate and expand. The exposed area of the hydrophilic matrix tablet can now hydrate and erode and release drug as is typical for hydrophilic matrix gum tablets but the remaining attached polymer film modifies (overall drug release changes, typically relative to uncoated materials, as a result of support platform generation) drug release from the coated portion of the tablet. Eventually, the entire tablet erodes away leaving two or more pieces of polymer film which may be visible in the dissolution liquid. Thus, these tablets which have been coated on all surfaces by spray coating with a drug release controlling polymer film coat over all exposed surfaces of the tablet are easily made with conventional tableting equipment, provide a desired lag time prior to drug release, generate support platforms in situ, release all drug in the desired time period, and provide nearly linear drug release as desired.

The n value for data in FIG. 6 is 0.95, and the data are quite linear.

EXAMPLE 4

Figure 7:
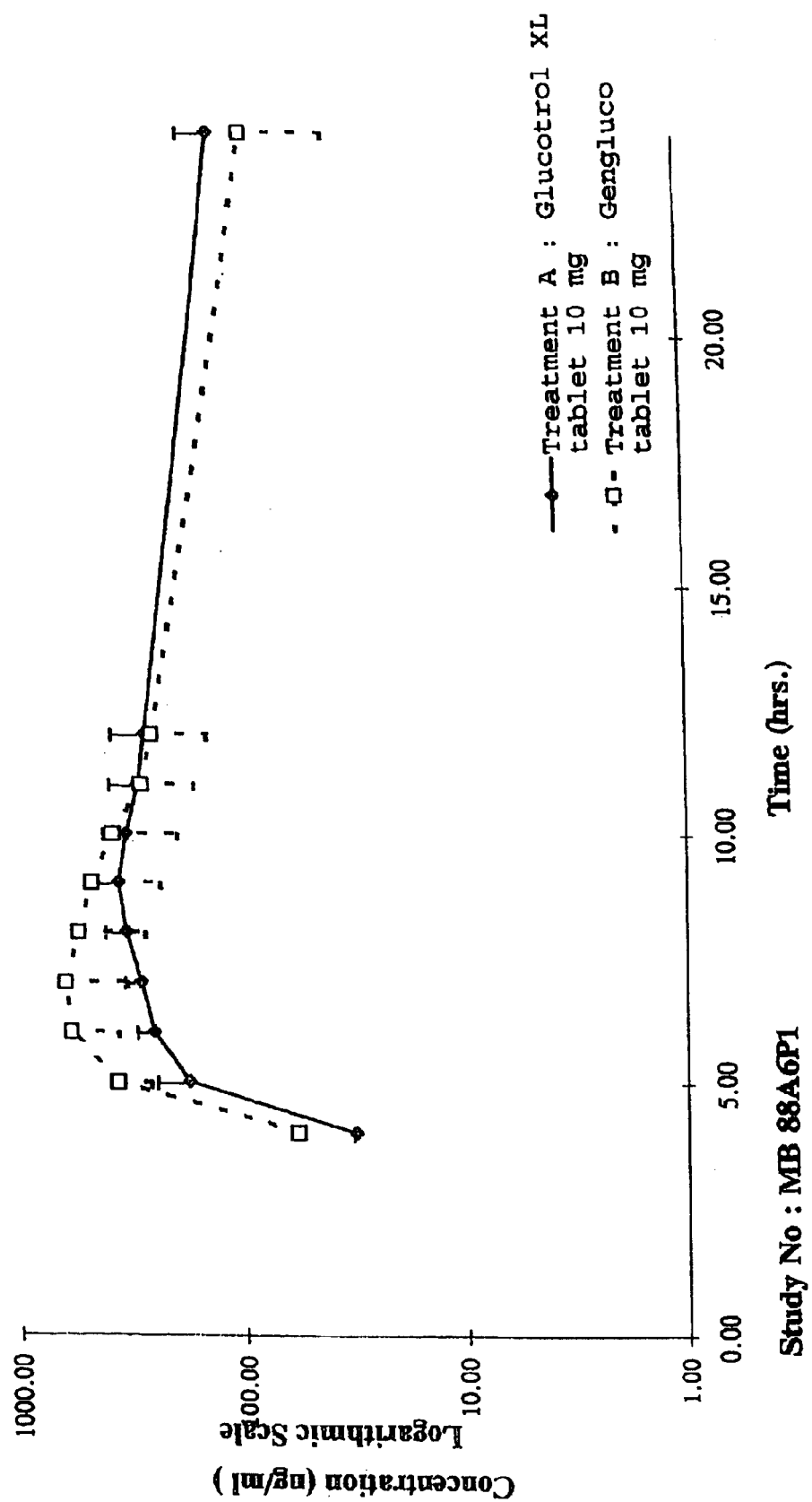
FIG. 7 is a graph showing average glipizide concentration in plasma following administration of Glucotrol XL osmotic pump tablets or Gengluco in situ platform generating tablets to human volunteers.

The tablets of Example 3 were administered to three subjects in Taiwan in a crossover bioavailability study with Glucotrol XL as a reference standard tablet. Average drug concentration vs. time curves for the two treatments are shown in FIG. 7. Peak drug concentration for the formulation of example 3 was higher than for Glucotrol XL, and the area under the curve from time zero to infinity for the two treatments was estimated to be within 10% of each other, which indicates that the extent of drug absorbed was essentially equivalent for the two products. Data in FIG. 7 show that tablets of this invention produce sustained release of an active ingredient following the lag time sufficiently such that the product maintains effective drug concentrations when administered to a human patient in a once daily regimen. For other therapeutic agents, it will immediately be recognized that with larger or smaller doses, as appropriate, and modification of formulation variables such as those taught herein, tablets of this invention provide sustained release of an active ingredient following the lag time which is sufficient such that the product maintains effective drug concentrations when administered to a human patient in a once or twice daily dosing regimen.

Figure 8:
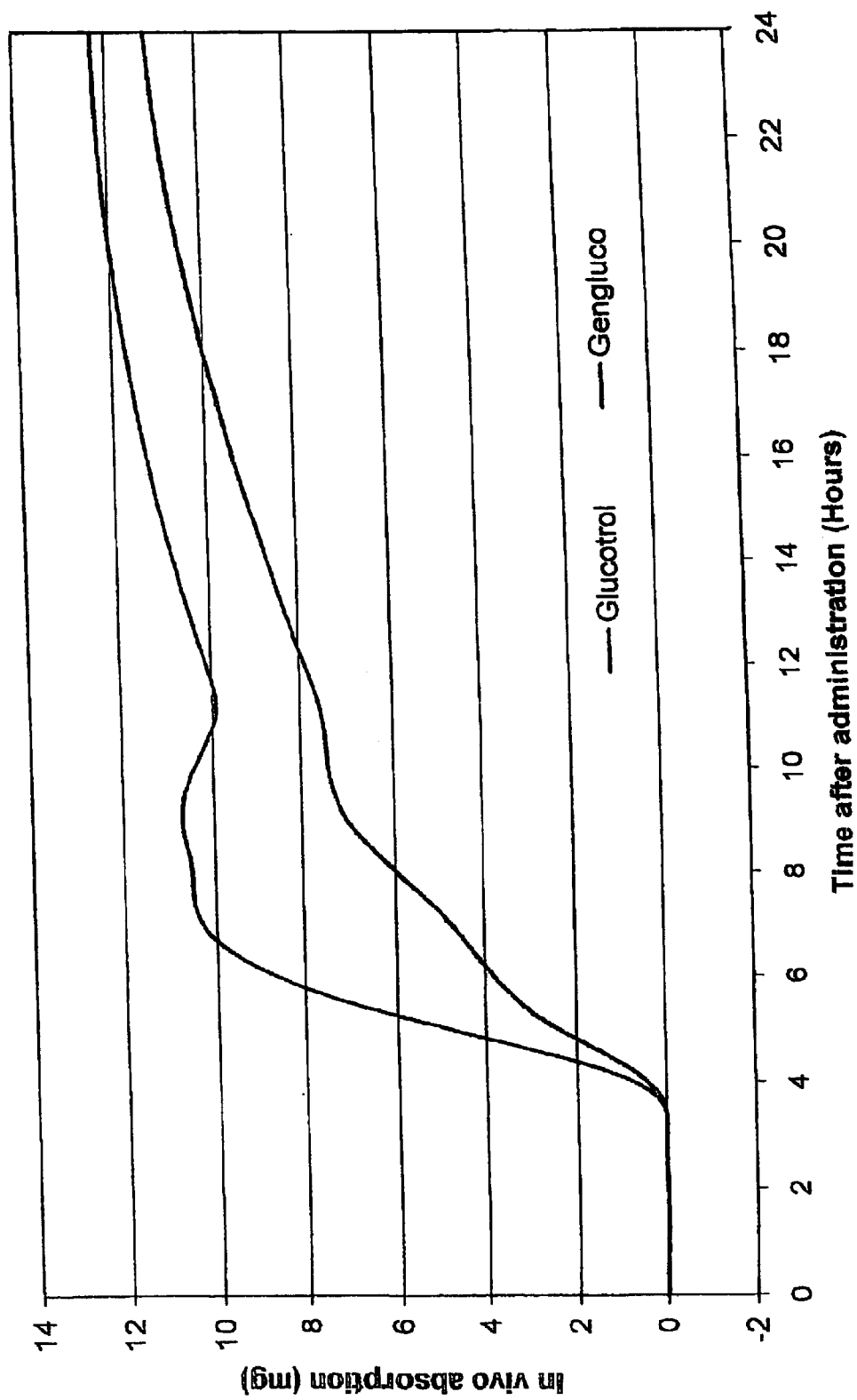
FIG. 8 is a graph showing in vivo absorption of glipizide from Glucotrol XL osmotic pump tablets or Gengluco in situ platform generating tablets administered to human volunteers, as obtained from deconvolution of the data in FIG. 6.

FIG. 8 presents the estimate of amount of drug absorbed vs. time as obtained from deconvolution of data in FIG. 7 using PCDECON (Gillespie W. R., PCDECON: Deconvolution for Pharmacokinetic Applications, July, 1992). FIG. 8 teaches that tablets of example 3 provide a lag time in vivo before drug is released, and result in quite linear drug absorption. FIGS. 7 and 8 teach that tablets of this invention can produce lag times of less than 4 hours. Longer or shorter lag times can be produced through formulation modification as indicated elsewhere herein. Drug release from Example 3 tablets is sustained in vivo, but not as much as for Glucotrol XL, even though drug release was nearly identical for the two products during in vitro dissolution testing.

EXAMPLE 5

Two different coated hydrophilic gum matrix tablets coded either as GSR20/GK910 or as GSR3/GK920 were prepared according to the following formulations.

| 10000 Tablets of Lot GSR20/GK910 Hydrophilic gum matrix tablets | | | |
|---|---|---|---|
| Glipizide | 10.00 mg | 2.22% | 100.00 gm |
| HPMC Type 2208 Viscosity 4000 | 67.50 mg | 15.00% | 675.00 gm |
| HPMC Type 2910 Viscosity 15 | 135.00 mg | 30.00% | 1350.00 gm |
| Avicel PH 102 | 172.00 mg | 38.22% | 1720.00 gm |
| Lactose Fast Flow | 52.00 mg | 11.56% | 520.00 gm |
| Glyceryl Behenate | 9.00 mg | 2.00% | 90.00 gm |
| Magnesium Stearate | 4.50 mg | 1.00% | 45.00 gm |
| Total: | 450.00 mg | 100.00% | 4500.00 gm |

Polymer Coating Formulation

Surelease Film Formula (Solid Ratio=80 surelease:20 Opadry white) 3% weight gain=168.8 g.

| | |
|---|---|
| Surelease E-7-19010 (25% Solid Content) | 540.0 g. |
| A 0.25% excess is used for compensation of spraying loss. | |
| Opadry White 31K58901 | 33.8 g |
| Purified Water | 551.3 g |
| Total: | 1125.0 g |

Manufacturing Steps

GSR20 (Lot: GK910)

Compression

1. Glipizide was mixed with HPMC 2910 (Viscosity 15) and was then sieved through a #40 sieve (425 mm).
2. Pass HPMC 2208 (Viscosity 4000), Avicel and Lactose through a #40 sieve (425 mm) into the mixture from step 1.
3. Mix the contents of step 2 in a V-blender for 25 minutes.
4. Mix Magnesium Stearate plus Glyceryl Behenate with an equal volume of the mixture of step 3 in a plastic bag, and pass through a #40 sieve (425 mm) into the remaining mixture from step 3.
5. Mix the contents of step 4 in a V-blender for 5 minutes.
6. Compress the bulk powder into 450 mg tablets. (HATA press; Diameter of 11.1 mm; thickness of 5.2 mm at the center and 3 mm at the edge.)

Coating

1. Disperse Opadry white E-7-19101 into stirring water, stir for 45 minutes.
2. Pour the suspension from step 1 into stirring Surelease suspension and make up to target weight with water.
3. Spray the coating solution onto core tablets made from Compression stage (weight gain 3%).

Spray application parameters are the same as in Example 3.

| 10000 Tablets of Lot GSR3/GK920 Hydrophilic gum matrix tablets | | | |
|---|---|---|---|
| Glipizide | 10.00 mg | 2.45% | 100.00 gm |
| HPMC Type 2208 Viscosity 100 | 346.67 mg | 84.97% | 3466.70 gm |
| Pectin | 43.33 mg | 10.62% | 433.30 gm |

-continued

| 10000 Tablets of Lot GSR3/GK920 Hydrophilic gum matrix tablets | | | |
|---|---|---|---|
| Magnesium Stearate | 8.00 mg | 1.96% | 80.00 gm |
| Total: | 408.00 mg | 100.00% | 4080.00 gm |

Surelease Film Formula (Solid Ratio=80% Surelease:20% Opadry white) 3% weight gain=153.0 g

| | |
|---|---|
| Surelease E-7-19010 (25% Solid Content) A 0.25% excess is used for compensation of spraying loss. | 489.6 g. |
| Opadry White 31K58901 | 30.6 g |
| Purified Water | 499.8 g |
| Total: | 1020.0 g |

GSR3 (Lot: GK920)
Compression
1. Glipizide was mixed with pectin and was then sieved through a #40 sieve (425 mm).
2. Pass HPMC 2208 (Viscosity 100) through a #40 sieve (425 mm) into the mixture of step 1.
3. Mix the contents of step 2 in a V-blender for 25 minutes.
4. Mix Magnesium Stearate and an equal volume of mixture of step 3 in a plastic bag and pass through a #40 sieve (425 mm) into step 3.
5. Mix the contents of step 4 in a V-blender for 5 minutes.
6. Compress the bulk powder into 408 mg tablets, slightly concave. (HATA press; Diameter of 11.1 mm; thickness of 4.7 mm)

Coating
1. Disperse Opadry white E-7-19101 into stirring water, stir for 45 minutes.
2. Pour the suspension from step 1 into stirring Surelease suspension and make up to target weight with water.
3. Spray the coating solution onto core tablets made from Compression stage (weight gain 3%).

Coating parameters were the same as for Example 3.

Figure 9:
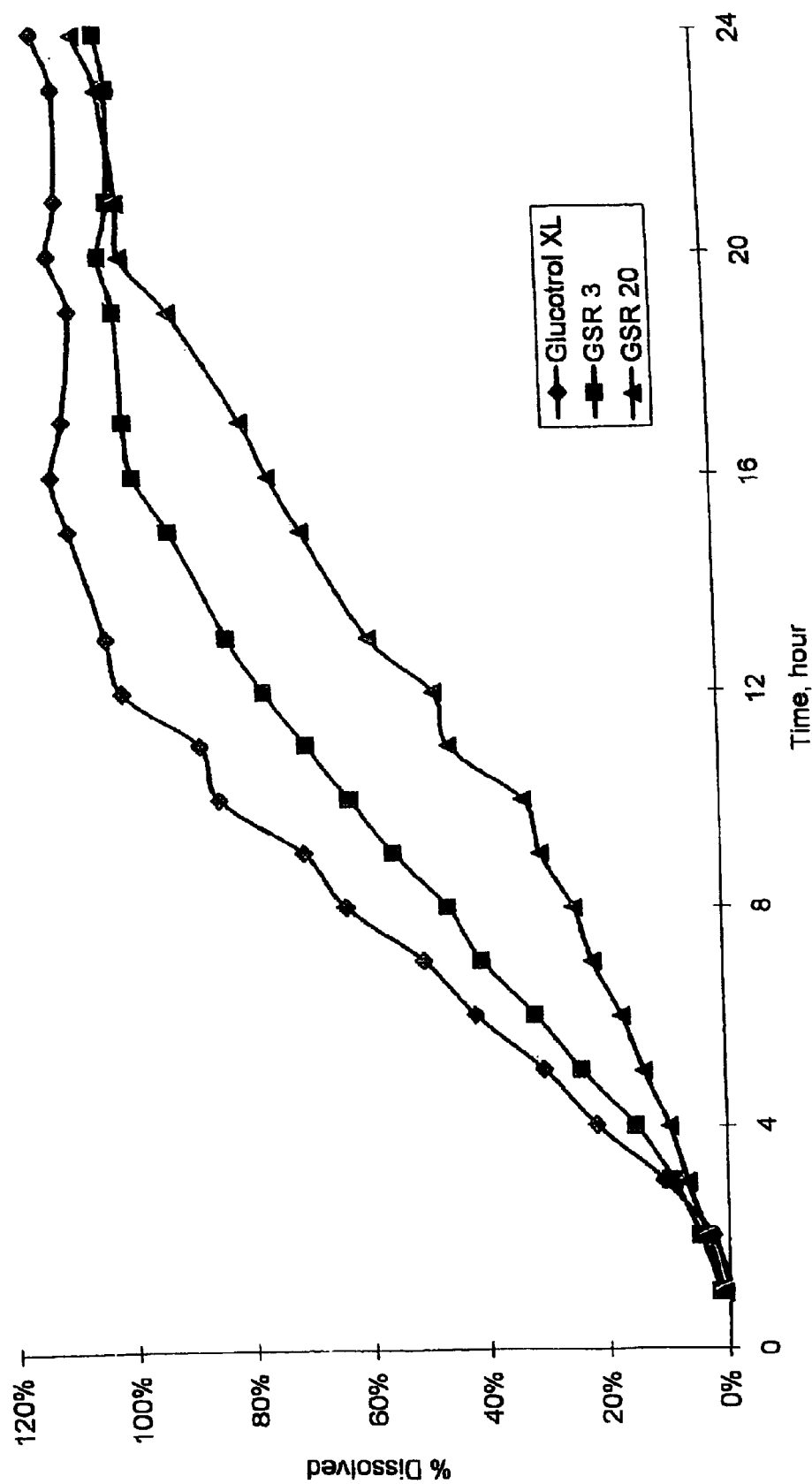
FIG. 9 is a graph showing percent drug (glipizide) release versus time from zero to 24 hours for Glucotrol XL and two different in situ support generating tablets (GSR3/GK920 and GSR20/GK910) in a USP dissolution test apparatus.

FIG. 9 shows dissolution data for glipizide release from Glucotrol XL, GSR3/GK920 and GSR20/GK910. The dissolution apparatus was USP V, paddle stirring at 100 RPM, in 800 ml of 0.05 M phosphate buffer, pH 7.4 at 37° C. Both formulations of the invention show a lag time equivalent to the lag time for Glucotrol XL, and both provide relatively zero order drug release with an n value of 0.7 for GSR3/GK920 and 0.9 for GSR20/GK910. Both new formulations release drug more slowly in the dissolution vessel than Glucotrol XL. These products were administered to six healthy subjects in a three way cross over study and average pharmacokinetic results are shown in the table below.

| | Glucotrol XL | GSR3/GK920 | GSR20/GK910 |
|---|---|---|---|
| Cmax (ng/ml) | 207 | 231 | 182 |
| $AUC_{0-48}$ | 1678 | 1407 | 1219 |

Total relative bioavailability of the drug from GSR20/GK910, which contains 45% HPMC, is only about 72%.

Tablet GSR3/GK920 contains much more hydrophilic gum, 95% of the weight of the core tablet, yet this tablet provides unexpectedly good relative bioavailability of the drug at about 84%.

Deconvolution results show that in vivo absorption from GSR3/GK920 and GSR20/GK910 each have a lag time for absorption of between about 1.0- and 2 hours, and absorption is sustained over more than 24 hours. In vivo lag times for GSR20/GK910 and GSR3/GK920 teach that the spray coated, in situ platform generating tablets described herein can provide a lag time in humans which mimics the lag time of an osmotic pump tablet. GSR3/GK920 data also teach that even with very high amounts (95% of the tablet weight in this case) of hydrophilic gum in the matrix tablet, bioavailability can be good. Bioavailability of GSR3/GK920 is 15% greater than from GSR20/GK910 which contains 50% less hydrophilic gum. That is, the formulation with the most gum gave the best bioavailability. It is believed that pectinase in the lower intestinal tract is beneficial in attacking the pectin portion of the tablet which results in more drug release from GSR3/GK920 than from GSR20/GK910. Enzymatic attack on pectin or guar gum has been used as a way to target drug delivery to the colon (U.S. Pat. Nos. 5,505,966 and 5,656,294). But, in these cases the objective is to avoid drug release in the stomach or in the upper small intestine, and use of these patents teach prevention of drug release prior to the time the delivery device reaches the colon. Tablets of guar gum plus drug plus HPMC or polyethylene oxide (PEO) in a PEO or HPMC/guar gum ratio of 0.08/1 allow drug dissolution in upper intestinal fluids, with no lag time, according to a first order and not a zero order process which differs from the invention reported herein (Syed A. Altaf, Karen Yu, Jagdish Parasarampuria, and David Friend, "Guar Gum-Based Sustained Release Diltiazem", Pharmaceutical Research, Vol.15, No.8, pp.1196–1200, 1998).

The HPMC/pectin ratio in GSR3/GK920 is 8:1 and the total hydrophilic gum content is 95%. Formulation Gengluco (Example 3) contains an HPMC/pectin ratio of 2:1 and has a total hydrophilic gum content of 45%. These examples in combination teach that the HPMC/pectin ratio and total amount of hydrophilic gum can be can be varied so as to provide complete bioavailability over a range of times from about 5 hours after the lag time (Examples 3 and 4) until well over 24 hours after the lag time. Percentage of drug absorbed from GSR3/GK920 and GSR20/GK910 respectively was 32% and 34% at 10 hours, 48% and 38% at 15 hours, and 54% and 42% at 20 hours. These amounts absorbed are thought to result from the combination of this invention involving multiple effects including coating parameters, hydrophilic gum amounts, type of hydrophilic gums, amount and ratio of pectin, and tablet shape to name a few factors. It will now be readily apparent to one skilled in the art that these factors can be changed as desired to obtain a programmed release of drug. Drug release rates mostly between, or faster or slower, than those exhibited by GSR20/GK910 and Gengluco, for example, can so be obtained.

Verapamil is an antihypertensive drug that is commercially available in an osmotic pump tablet (trade name Covera HS) or in a hydrophilic matrix tablet (trade name Calan SR). Calan SR is coated with a glossy water soluble film coat which rapidly dissolves and has essentially no effect on drug release. Cutting the Calan SR tablet in half has very little effect on the sustained release characteristics of drug from this tablet. Dissolution of verapamil from these two commercial tablets is not at the same rate which is expected since one is an osmotic pump and the other is a hydrophilic matrix tablet, and these products are not approved by FDA as interchangeable. There is a lag time for drug release from Covera HS, and there is essentially no effective lag time for drug release from Calan SR.

Figure 10:
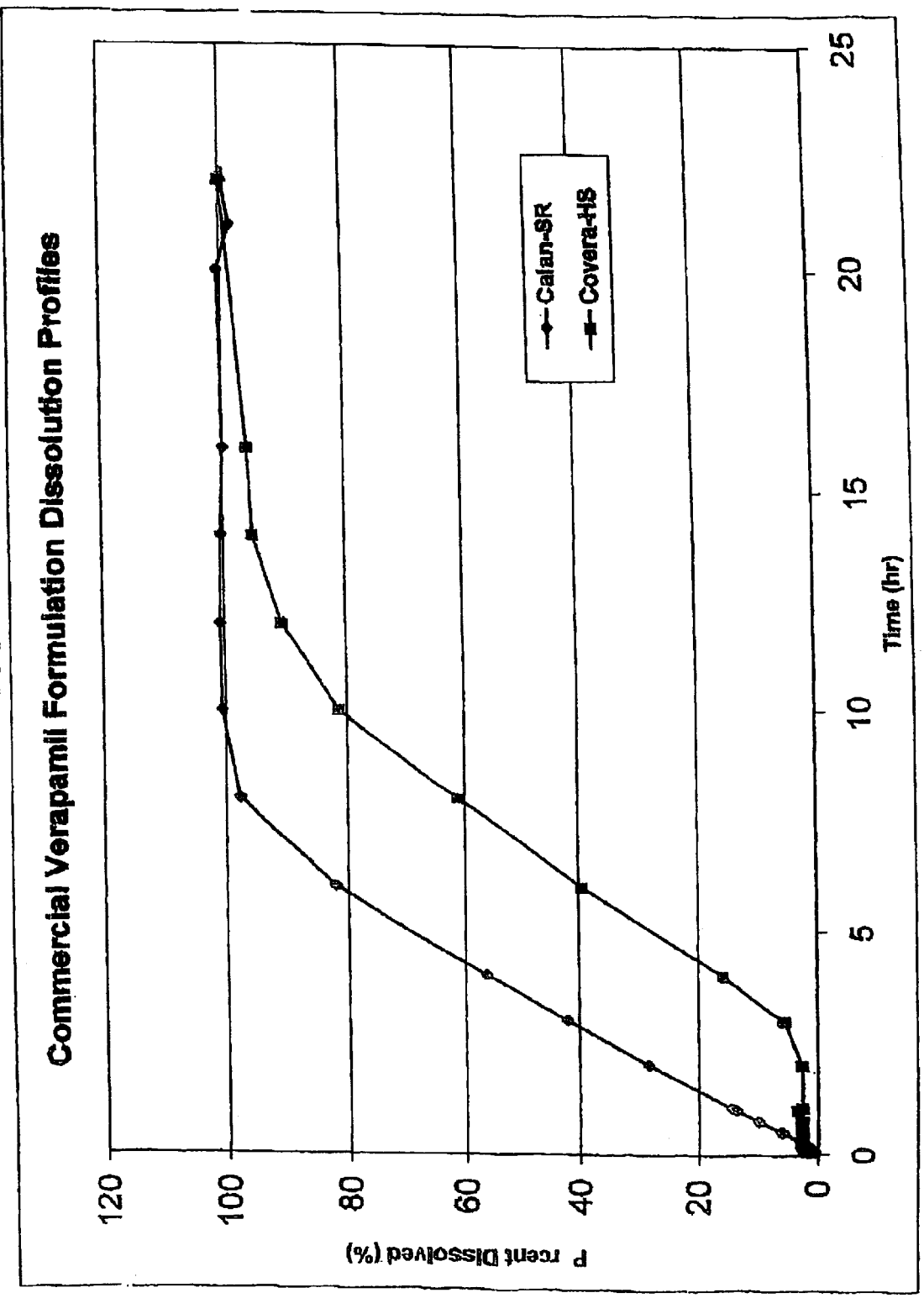
FIG. 10 is a dissolution versus time curve of two commercial verapamil formulations.
Figure 11:
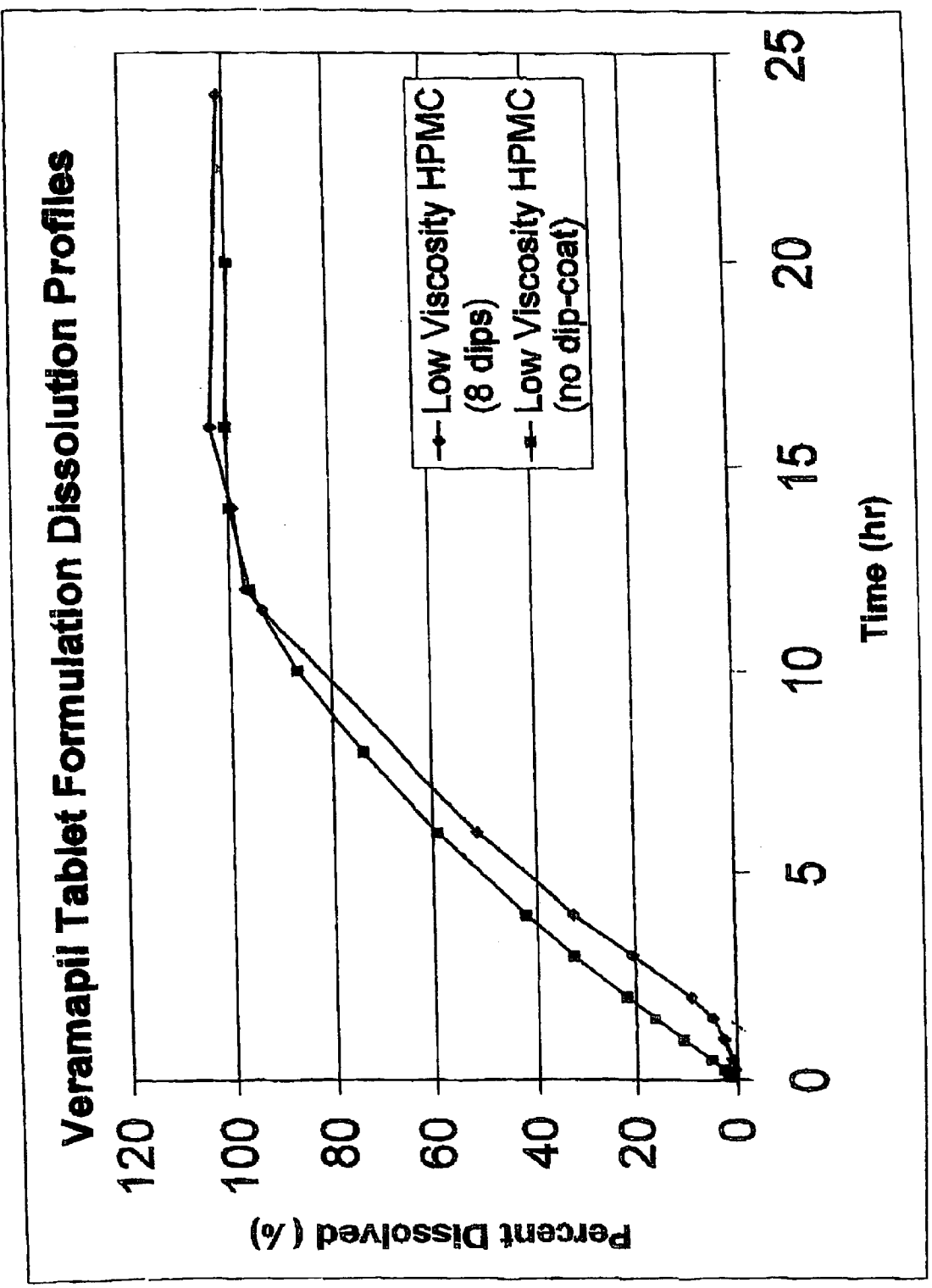
FIG. 11 is a dissolution versus time curve of a Verapamil formulation comprising coated and uncoated low viscosity HPMC tablets.

FIG. 10 shows dissolution of verapamil in USP paddle stirring equipment from the commercially available osmotic pump tablet "Covera-HS" compared to the hydrophilic matrix tablet "Calan-SR". FIG. 11 shows release of verapamil from an uncoated hydrophilic matrix tablet and a dip coated tablet which generates an in situ support platform as described herein. It is clear there is essentially no lag-time for release from the uncoated tablet, and there is a lag time for drug release from the tablet which has been dip coated 8 times over the entire surface, and allowed to dry between coatings, using the formulations in the table below. Longer lag times can be obtained with additional coating thickness produced by additional dippings. The lag time in FIG. 11 is about 1–1.3 hours as determined by extrapolation to the x axis of the % drug released at times 2, 3, and 4 hours which are the first nearly linear three time points following about 5% drug release which occurs at about 1.5 hours, which could also be considered the lag time.

It can also be seen in FIG. 11 that the drug release rate from the in situ support platform generating tablet is more rapid from about time one or two hours until 12 hours than from the uncoated tablet. This is clear since the amount released reaches 90% at about the same time, but the amount released from these tablets differed by about 10% at about times one or two hours. This faster release rate effect is very clear in FIG. 12, which shows dissolution of verapamil from another formulation of this invention (see table below for formulation ingredients).

| Verapamil tablet formulation: | | |
|---|---|---|
| Ingredients | weight (mg) | percent (%) |
| verapamil HCl | 121.4 | 27.27 |
| HPMC | 182 | 40.91 |
| Pectin | 30.3 | 6.82 |
| avicel | 101 | 22.73 |
| Mg stearate | 10 | 2.27 |

NOTE: The same formulation ingredients and quantities were used for the tablets associated with FIG. 11 and for the tablets associated with FIG. 12 except that HPMC 15 cps was used for the tablets associated with FIG. 11 and HPMC 4K was used for the tablets associated with FIG. 12. The formulation for the coating solution in both cases was Opadry (2.7 g), Surelease (17 ml), and water (80 ml). The tablet was round, flat-faced with a diameter of 10 mm. Thus, the belly band to height ratio was 1.0.

Figure 12:
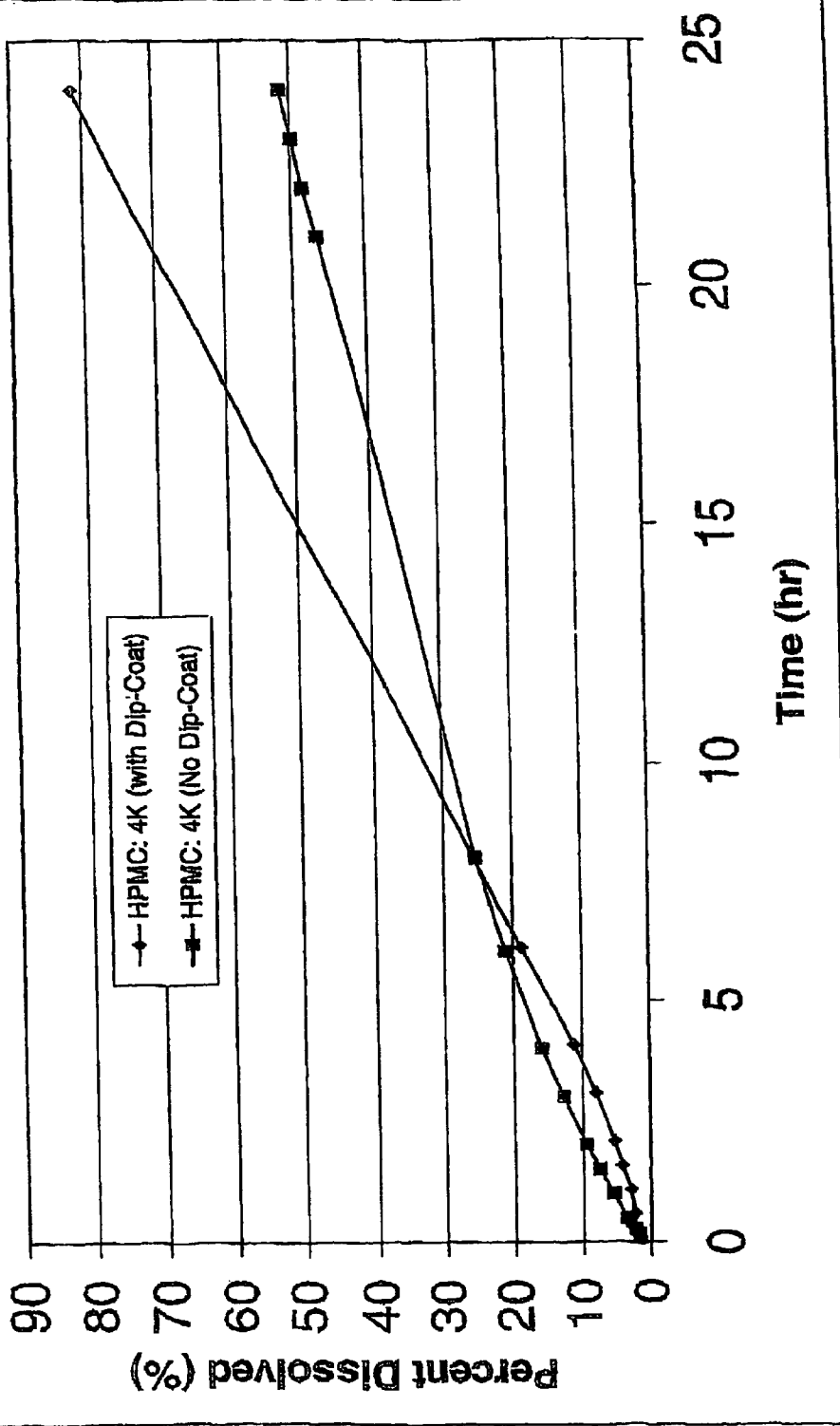
FIG. 12 is a dissolution versus time curve of a Verapamil formulation comprising coated and uncoated HPMC 4K.
Figure 14A:
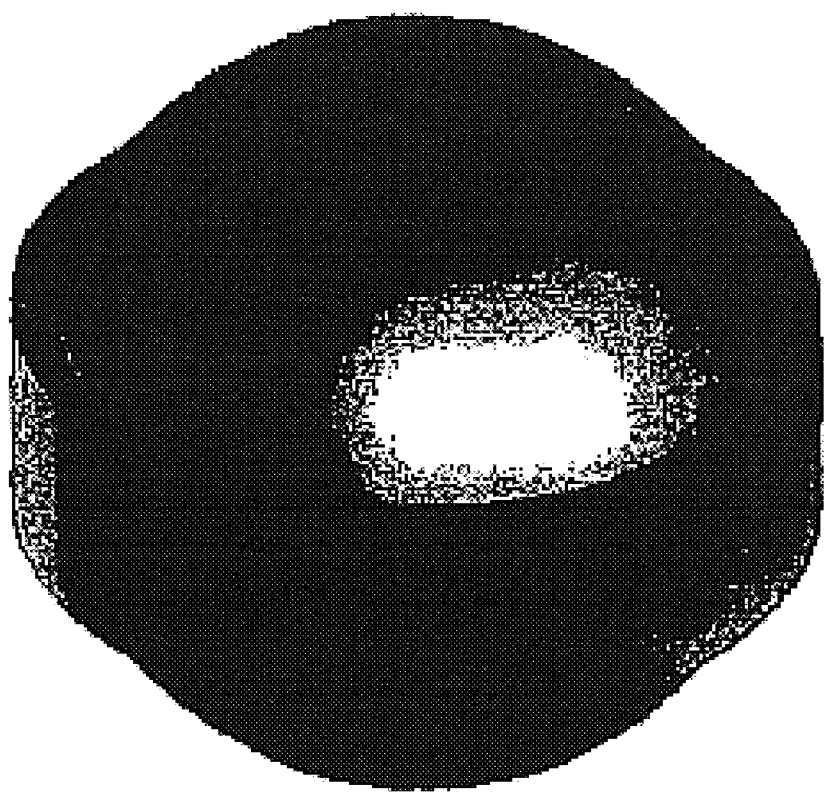
FIGS. 14A–14E are schematic drawings illustrating different shaped tablets which were used to produce the data represented by FIG. 13 and which can generate variable areas of exposure and coverage by in situ generation of support platforms.
Figure 14B:
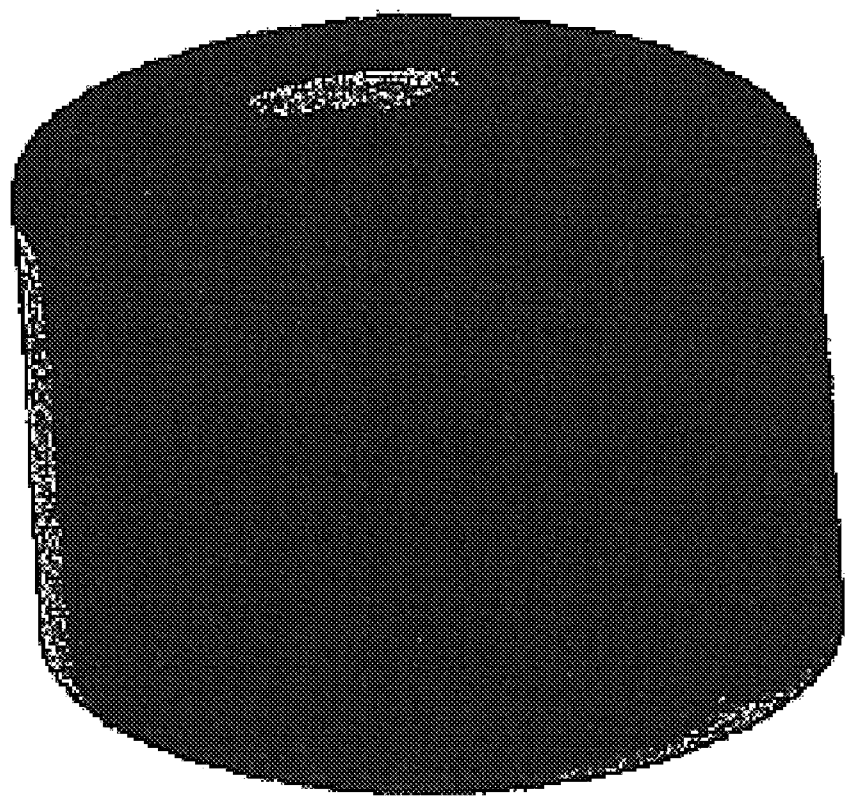
Figure 14C:
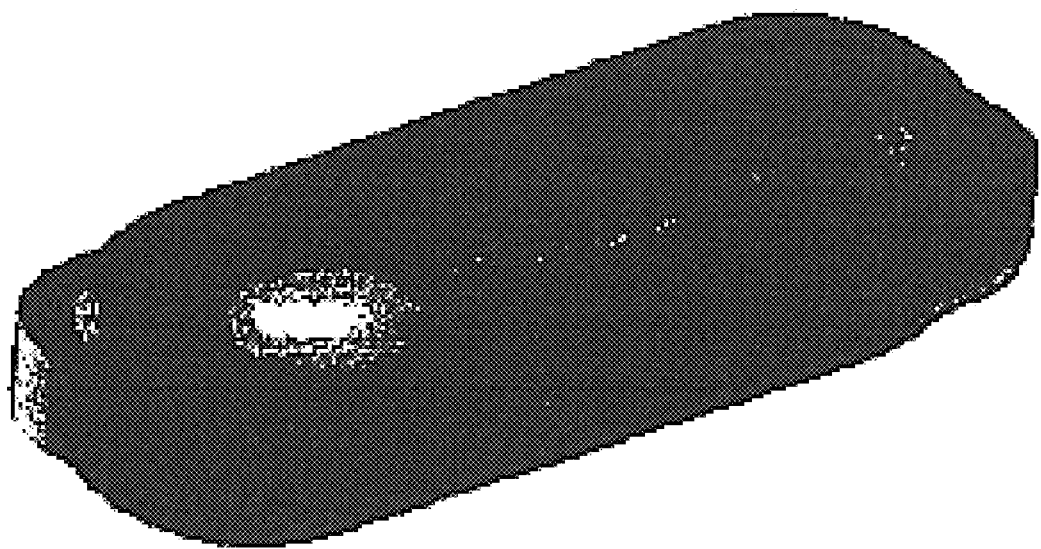
Figure 14D:
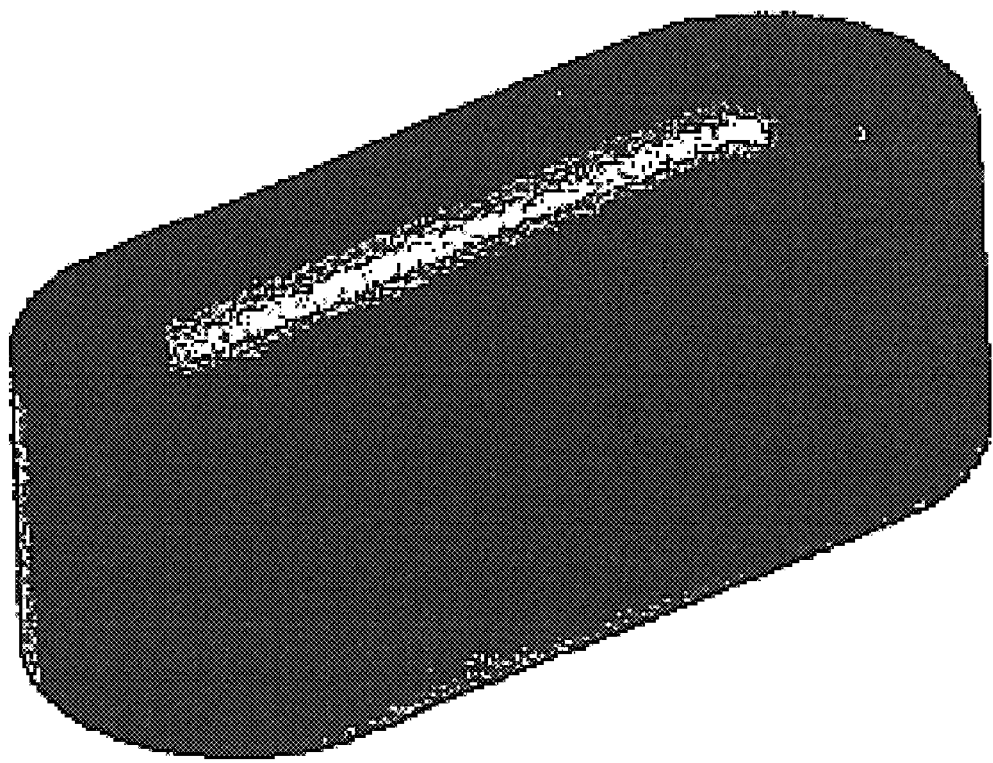
Figure 14E:
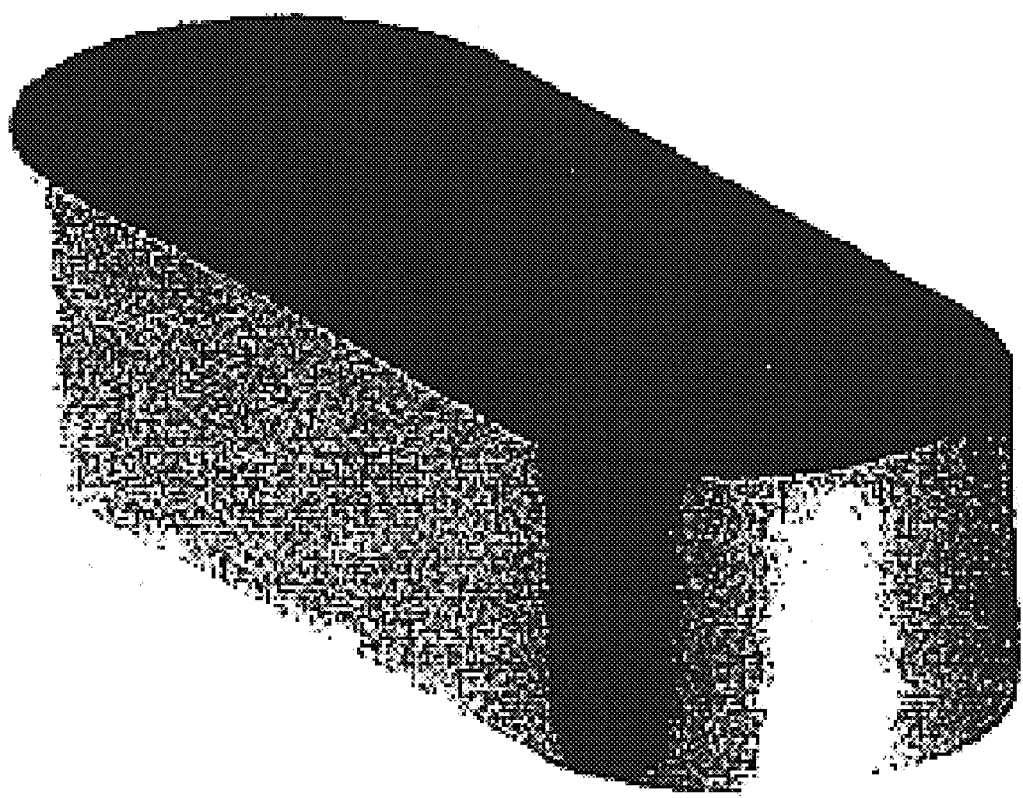

It can be seen in FIG. 12 that only about 50% of drug was released in 24 hours from uncoated tablets, and there was no lag time. For tablets dip coated 8 times over the entire surface there is a lag time, and drug release was about 80% at time 24 hours, which is a more rapid release rate from time after 4 hours than for the uncoated tablet. It is quite surprising that coating with a slow release polymer film over the entire surface of this slow release tablet results in an increased rate of drug release following the lag time rather than a decreased rate of drug release. This effect is quite useful since drug release is more nearly zero-order and more nearly complete in 24 hours suggesting an improved relative bioavailability. The cause of this surprising finding is not understood but it is not dependent on pectinase since there was no pectinase used in these experiments. These results show some of the drug release programming features of this invention in that core tablets containing an expandable material, such as hydrophilic gums or mixtures of hydrophilic gums of different expansion characteristics and different viscosity behaviors upon exposure to an aqueous environment, can now be selected to obtain surprising and desired drug release patterns when the core tablet has a rupturable coating comprising a rate release modifying membrane.

FIG. 13 shows the effect of tablet shape as an additional drug release programming feature of this invention. Five different tablets, each one containing the same formulation as shown in the table below but each tablet having a different shape, were prepared according to the invention disclosed herein.

| Hydrophilic tablet core composition | | |
|---|---|---|
| Ingredients | Composition (%) | Amount per Tablet (mg) |
| Verapamil Hydrochloride | 27.27 | 240 |
| Hydropropylmethylcellulose 15 cps | 40.90 | 360 |
| Pectin | 6.82 | 60 |
| Avicel PH 101 | 22.73 | 200 |
| Magnesium Stearate | 2.27 | 20 |
| Total | 99.99 | 880 |
| Coating Solution Formulation | | |
| Ingredients | Composition | |
| Surelease (24.8% w/w Solid) | 64 ml (63.95 g solid) | |
| Opradry | 10.125 g | |
| Talc | 21.307 g | |
| Deionized Water | 300 ml | |

The shapes were round biconcave, round biconvex, elongated biconcave, elongated biconvex, and flat-faced caplet as shown in FIG. 14. The results (FIG. 13) show that a lag time and zero-order drug release can be obtained, and a controlled release over a programmed but variable time is obtained. This programmed control is obtained with a low expansion, low viscosity, hydrophilic polymer (HPMC 15 cps). The drug release rate can be programmed to be any of a wide variety of rates which are very different, and may be zero order or nonzero order, depending on what is desired. In one case the drug release is complete in 12 hours and in others release is essentially continuous following the lag time over 24 hours.

In one case the drug release rate (round biconvex tablet) from 18–24 hours is much faster then the drug release rate when compared to time zero to 18 hours. This overall release pattern illustrated for round biconvex tablets is referred to herein as a "concave upward" curve, and is not expected for hydrophilic matrix tablets. For this particular tablet of the disclosed larger invention, less than 15 percent of the drug is released in less than 10 hours and 70% is dissolved in 24 hours. Tablets with this type of release pattern (lag time followed by "concave upward" release) will be particularly useful for some drugs, such as would be useful for colonic drug delivery. FIG. 13 shows the tablets of this invention can provide sustained release of an active ingredient following a lag time which is sufficient to provide therapeutically effective active ingredient concentrations when administered in a once- or twice-daily dosing regimen. During dissolution of the tablets illustrated by FIG. 14, in every case the rate release modifying membrane ruptured adjacent to or in the belly band area of the tablet upon exposure to the aqueous dissolution fluid, and then produced a support platform for drug delivery as described herein. Following coat rupture, the belly band is the primary area exposed directly to hydrating fluids by rupture of the rate release modifying membrane even though there may be some cracks, breakage, or rupture in some areas of the remaining support platform. FIG. 14 illustrates that the belly band area of the depicted tablets varies from only a fraction of the total tablet height at the tallest point for the convex tablets to 100% (1.0) of the tablet height measured at the tallest point for the concave tablets. The belly band is even greater than 1.0 of the distance between the bottoms of each concave surface measured through the center of the concave tablets. Thus, another programmable feature of this invention is the belly band size and shape relative to the shape and size of the tablet. Still another programmable feature is the use of tablets of concave, flat, or convex shapes whether round, oval, or elongated, and combinations of shapes and belly band designs. Square and triangular tablets as well as other shapes can be used.

Verapamil tablets made according to the invention described herein exhibit a lag time for drug release, which release can be effectively identical to that of Covera-HS, or can be longer if desired, and drug release can be essentially zero order with n=0.85 or greater in either case from after the lag time until 85% of the drug is released in a dissolution test, and time for total drug release can be controlled between less than 10 hours to more than 24 hours, and programmed formation of support platforms occurs, and a platform can be seen to be generated in situ in a dissolution test, and may still be visible and attached to the non-belly band area of the tablet after 16 hours or more.

Examples 3, 4 and 5 show that a tablet dosage form of this invention can provide programmed release of an active ingredient from a core portion containing an active ingredient and an expanding material, which is only partially responsible for providing the programmed release, when the core portion is coated over the entire surface by spray coating or dip coating with a rate release controlling membrane, which is also only partially responsible for providing the programmed release; and the programmed release includes a lag time for release of active ingredient from the core portion followed by sustained release of active ingredient when the tablet expands sufficiently during use or testing to rupture the rate release controlling membrane and produce a support platform in situ.

Coat failure has been abhorrent to drug product formulators, but programmed and selective coat rupture will now be recognized as desirable in this invention, and a factor which can be controlled to influence rate of drug release. In a preferred embodiment, the coat will selectively rupture (fail) in dissolution fluid in less than about 4 hours mostly around the belly band area (vertical surfaces) of the tablet, and remain attached to act as a support platform on about 50% or more of the horizontal surfaces of the tablet.

Tablet shape can be modified to control both the amount of surface protected by the residual support platform and the amount of core tablet exposure following coat failure, and to influence the rate of coat failure. Coat composition can be formulation controlled by one skilled in the art to be sufficiently thin and brittle to rupture appropriately and to still be capable of providing support platforms. One skilled in the art will now readily recognize that variation in any or all of these factors can be combined with variations in the amount and types of hydrophilic gums and the ratios of gums to program a desired drug release. And, one skilled in the art will recognize that with this now disclosed invention, there are a very broad range of release effects which can be controlled with a relatively few formulation modifications such that this invention has ready application for active agents of a very wide range of solubilities, from very soluble to very insoluble. And, it will be recognized that the presence of the support platform following coat rupture provides a mechanical barrier and at least partial protection from the erosion action created by peristaltic and grinding motion of the gastrointestinal tract. Parameters of the coat which generates the support platform such as thickness, tensile strength, flexibility, porosity, strength of binding to the tablet, and resistance to drug diffusion, to name a few, can all be varied either alone or in combination with other parameters of the formulation such as shape, excipients, and others so that the lag time and the platform barrier effects can be modified as desired. Thus, tablets of this invention will be more resistant to peristaltic action and gastrointestinal erosion effects than hydrophilic matrix tablets known in the art, and thus release of active ingredient can now be less affected by administration with meals compared to what is known (Bertil Abrahamsson, Magne Alpsten, Gjom Bake, Ulf Jonsson, Maria Eriksson-Lepkowska and Annhild Larsson, "Drug Absorption from nifedipine hydrophilic matrix extended-release (ER) tablet-comparison with an osmotic pump tablet and effect of food", Journal of Controlled Release, 52, pp. 301–310 (1998)).

The present application has been described with reference to examples of preferred embodiments. It will be apparent to those of ordinary skill in the art that changes and modifications may be made without departing from this invention.

I claim:

1. A sustained release, platform forming tablet, comprising:
   one or more active ingredients;
   a mixture of hydrophilic gum polymers where the mixture comprises between about 40% and 95% by dry weight of the tablet ingredients, the mixture comprising at least one hydrophilic gum polymer, which is modified by enzymes in the intestinal tract;
   at least one excipient, which promotes powder mixture flow;
   a belly band comprising at least one active ingredient; and
   a spray coating over an external surface of the tablet, the coating comprising a rupturable rate release controlling membrane that ruptures in a subject's gastrointestinal tract.

2. The tablet according to claim 1 wherein the hydrophilic gum polymer is pectin.

3. A spray-coated tablet, which exhibits a lag time for active ingredient dissolution, comprising:
   glipizide;
   a mixture of hydrophilic gum polymers comprising at least one hydrophilic gum polymer, which is modified by enzymes in the intestinal tract;
   a belly band comprising glipizide; and
   a rate release controlling membrane overcoating the mixture.

4. The tablet according to claim 3 wherein the hydrophilic gum polymer is pectin.

5. The tablet according to claim 3 where the rate controlling membrane is ethyl cellulose or a methacrylate polymer.

6. The tablet according to claim 3 where at least one hydrophilic gum is hydroxypropyl methyl cellulose, the hydrophilic gum polymer, which is modified by enzymes in the intestinal tract, is pectin, and the rate controlling membrane comprises ethyl cellulose or a methacrylate.

7. The tablet of claim 3 where, during hydration with aqueous fluids, the hydrophilic polymer gum core tablet swells and the rate controlling membrane ruptures in a subject's gastrointestinal tract, breaks away from part of the tablet and exposes portions of the hydrophilic gum polymer core tablet, and remains attached to portions of the tablet providing a support platform for at least two hours after initial breaking of the polymer release rate controlling film occurs.

8. The tablet according to claim 3 where the belly band is between about 1 and about 8 mm thick and the length of the tablet is at least 8 mm.

9. The tablet according to claim 8 where the belly band of the tablet is equal to or larger than vertical height of the tablet as measured at the center of the tablet.

10. The tablet according to claim 3 having a first rate controlling membrane, and wherein the first rate controlling membrane has been over coated with a second rate release controlling membrane, at least one of the rate release controlling membranes being an enteric coating membrane.

11. The tablet according to claim 3 where the rate controlling membrane has been over coated with one or more active ingredients, which may be the same or different from the active ingredients in the core tablet, and wherein the release of the active ingredient may or may not exhibit a lag time for active ingredient dissolution.

12. The tablet according to claim 3 where dissolution of the active ingredient is approximately zero order in that the calculated n value for average dissolution results after the lag time is greater than 0.70 from time of 10% drug released until time of 75% drug released.

13. The tablet according to claim 3 where dissolution of the active ingredient is approximately zero order in that the calculated n value for average dissolution results after the lag time is greater than 0.85 from time of 5% drug released until time of 85% drug released.

14. The tablet according to claim 3 wherein dissolution of the active ingredient is approximately zero order in that the calculated n value for average dissolution results after the lag time is greater than 0.70 from time of 10% drug released until time of 75% drug released.

15. The dosage form of claim 3 wherein dissolution of the active ingredient is approximately zero order in that the calculated n value for average dissolution results after the lag time is greater than 0.85 from time of 5% drug released until time of 85% drug released.

16. A tablet, which exhibits a lag time for active ingredient dissolution, comprising:
   one or more active ingredients;
   a belly band comprising at least one active ingredient;
   a core comprising a mixture of hydrophilic gum polymers comprising between about 40% and about 95% by dry weight of all tablet ingredients, the mixture comprising at least one hydrophilic gum polymer, which is modified by enzymes in the intestinal tract and at least one excipient, which promotes powder mixture flow and attracts water; and
   an outer rupturable coating that ruptures in a subject's gastrointestinal tract, the coating comprising a rate release controlling membrane.

17. The tablet of claim 16 wherein the hydrophilic gum polymer which, is modified by enzymes in the intestinal tract is pectin.

18. A barrier coated tablet, which generates a support platform in situ, comprising:
   a core defining a belly band comprising an active ingredient; and
   an outer rupturable coating that ruptures in a subject's gastrointestinal tract, the coating comprising a rate release controlling membrane, such that the barrier coated tablet has a drug dissolution versus time curve with a lag time of between 0.5 and 3 hours, an n value of 0.85 or greater, and where a k value is between 0.04 and 0.25.

19. A barrier coated tablet, which generates a support platform in situ, comprising:
   a core defining a belly band comprising an active ingredient; and
   an outer rupturable coating that ruptures in a subject's gastrointestinal tract, the coating comprising a rate release controlling membrane, such that the barrier coated tablet has a drug dissolution versus time curve with a lag time of between 0.5 and 3 hours, an n value of 0.85 or greater, and the k value is between 0.05 and 0.1.

20. A tablet, comprising:
   a core comprising an active ingredient, a belly band comprising the active ingredient, and an enzymatically modifiable, expandable material, which expands upon exposure to an aqueous environment; and
   an outer rupturable rate release modifying membrane that ruptures in a subject's gastrointestinal tract, the tablet providing active ingredient release over at least a 16-hour period.

21. A tablet having a drug-delivery lag time, comprising:
   a core comprising an active ingredient, a water-soluble modifier gum and at least one second expandable gum, which expands upon exposure to an aqueous environment;
   a belly band comprising the active ingredient; and
   an outer rupturable rate release modifying membrane that ruptures in a subject's gastrointestinal tract over coating the core.

22. The tablet according to claim 21 where the active ingredient is glipizide.

23. A spray coated tablet according to claim 21.

24. The tablet of claim 16 where, during hydration with aqueous fluids, the core swells and ruptures the rate controlling membrane, which breaks away from part of the tablet and exposes portions of the core, and remains attached to portions of the tablet providing a support platform for at least two hours after initial breaking of the rate release controlling membrane.

25. The tablet of claim 18 where, during hydration with aqueous fluids, the core swells and ruptures the rate controlling membrane, which breaks away from part of the tablet and exposes portions of the core, and remains attached to portions of the tablet providing a support platform for at least two hours after initial breaking of the rate release controlling membrane.

26. The tablet of claim 19 where, during hydration with aqueous fluids, the core swells and ruptures the rate controlling membrane, which breaks away from part of the tablet and exposes portions of the core, and remains attached to portions of the tablet providing a support platform for at least two hours after initial breaking of the rate release controlling membrane occurs.

27. The tablet of claim 21 where, during hydration with aqueous fluids, the core swells and ruptures the rate controlling membrane, which breaks away from part of the tablet and exposes portions of the core, and remains attached to portions of the tablet providing a support platform for at least two hours after initial breaking of the rate release modifying membrane occurs.

28. The tablet according to 18 where dissolution of active ingredient from the outer rupturable coating and dissolution of active ingredient from the core is approximately zero order in that the calculated n value for average dissolution is greater than 0.70 from time of 10% drug released until time of 75% drug released.

29. The tablet according to claim 18 where dissolution of active ingredient from the core is approximately zero order, independent of drug release from the outer rupturable coating, in that the calculated n value for average dissolution is greater than 0.70 from time of 10% drug released until time of 75% drug released.

30. The tablet according to claim 18 where dissolution of the active ingredient from the outer rupturable coating plus dissolution of active ingredient from the core is approximately zero order in that the calculated n value for average dissolution result is greater than 0.85 from time of 5% drug released until time of 85% drug released.

31. The tablet according to claim 18 where dissolution of the active ingredient from the core is approximately zero order, independent of drug release from the outer rupturable coating, in that the calculated n value for average dissolution result is greater than 0.85 from time of 5% drug released until time of 85% drug released.

32. The tablet according to 19 where dissolution of active ingredient from the outer rupturable coating and dissolution of active ingredient from the core is approximately zero order in that the calculated n value for average dissolution is greater than 0.70 from time of 10% drug released until time of 75% drug released.

33. The tablet according to claim 19 where dissolution of active ingredient from the core is approximately zero order, independent of drug release from the outer rupturable coating, in that the calculated n value for average dissolution is greater than 0.70 from time of 10% drug released until time of 75% drug released.

34. The tablet according to claim 19 where dissolution of the active ingredient from the outer rupturable coating plus dissolution of active ingredient from the core is approximately zero order in that the calculated n value for average dissolution result is greater than 0.85 from time of 5% drug released until time of 85% drug released.

35. The tablet according to claim 19 where dissolution of the active ingredient from the core is approximately zero order, independent of drug release from the outer rupturable coating, in that the calculated n value for average dissolution result is greater than 0.85 from time of 5% drug released until time of 85% drug released.

36. A method for administering an active ingredient, comprising:
providing a tablet comprising one or more active ingredients, a mixture of hydrophilic gum polymers where the mixture comprises between about 40% and 95% by dry weight of tablet ingredients, the mixture comprising at least one hydrophilic gum polymer, which is modified by enzymes in the intestinal tract, at least one excipient, which promotes powder mixture flow, a belly band comprising at least one active ingredient, and a spray coating over the external surface of the tablet, the coating comprising a rupturable rate release controlling membrane that ruptures in a subject's gastrointestinal tract; and
administering the tablet to a subject.

37. A method for administering an active ingredient, comprising:
providing a tablet comprising glipizide, a belly band comprising glipizide, a mixture of hydrophilic gum polymers comprising at least one hydrophilic gum polymer, which is modified by enzymes in the intestinal tract, and a rate release controlling membrane overcoating the mixture, the membrane rupturing in a subject's gastrointestinal tract; and
administering the tablet to a subject.

38. A method for administering an active ingredient, comprising:
providing a tablet comprising one or more active ingredients, a belly band comprising at least one active ingredient, a mixture of hydrophilic gum polymers comprising between about 40% and about 95% by dry weight of all tablet ingredients, the mixture comprising at least one hydrophilic gum polymer, which is modified by enzymes in the intestinal tract and at least one excipient, which promotes powder mixture flow and attracts water, and an outer rupturable coating that ruptures in a subject's gastrointestinal tract, the coating comprising a rate release controlling membrane; and
administering the tablet to the subject.

39. A method for administering an active ingredient, comprising:
providing a barrier coated tablet defining a belly band comprising the active ingredient, which generates a support platform in situ, and a drug dissolution versus time curve with a lag time of between 0.5 and 3 hours, an n value of 0.85 or greater, and where a k value is between 0.04 and 0.25; and
administering the tablet to a subject.

40. A method for administering an active ingredient, comprising:
providing a barrier coated tablet, which generates a support platform in situ, the barrier coated tablet defining a belly band comprising an active ingredient, having a drug dissolution versus time curve with a lag time of between 0.5 and 3 hours, an n value of 0.85 or greater, and where a k value is between 0.05 and 0.1; and
administering the tablet to a subject.

41. A method for administering an active ingredient, comprising:
providing a tablet having a core comprising an active ingredient, a belly band comprising the active ingredient, a water-soluble modifier gum and at least one second expandable gum that expands upon exposure to an aqueous environment, and an outer rupturable rate release modifying membrane, which ruptures in a subject's gastrointestinal tract, over coating the core; and
administering the tablet to the subject.

* * * * *